US008440441B2

(12) United States Patent
Bluchel et al.

(10) Patent No.: US 8,440,441 B2
(45) Date of Patent: May 14, 2013

(54) METHOD OF PREPARING A SUBSTRATE FOR IMMOBILIZATION OF FUNCTIONAL SUBSTANCES THEREON AND THE SUBSTRATE OBTAINED THEREFROM

(75) Inventors: Christian Bluchel, Singapore (SG); Yanmei Wang, Singapore (SG)

(73) Assignee: Temasek Polytechnic (SG)

( * ) Notice: Subject to any disclaimer, the term of this patent is extended or adjusted under 35 U.S.C. 154(b) by 0 days.

(21) Appl. No.: 13/580,055

(22) PCT Filed: Feb. 18, 2011

(86) PCT No.: PCT/SG2011/000069
§ 371 (c)(1),
(2), (4) Date: Nov. 2, 2012

(87) PCT Pub. No.: WO2011/102807
PCT Pub. Date: Aug. 25, 2011

(65) Prior Publication Data
US 2013/0048559 A1    Feb. 28, 2013

(30) Foreign Application Priority Data

Feb. 19, 2010    (GB) .................................. 1002824.9

(51) Int. Cl.
*C12N 11/02*    (2006.01)
*C02F 1/00*    (2006.01)

(52) U.S. Cl.
USPC ............ 435/177; 435/180; 435/181; 210/632

(58) Field of Classification Search .................. 435/177, 435/180, 181; 210/632
See application file for complete search history.

(56) References Cited

U.S. PATENT DOCUMENTS

| 3,952,053 | A | * | 4/1976 | Brown et al. ................ 562/483 |
| 4,415,663 | A | | 11/1983 | Symon et al. |
| 4,576,928 | A | | 3/1986 | Tani et al. |
| 4,915,839 | A | | 4/1990 | Marinaccio et al. |
| 6,946,527 | B2 | | 9/2005 | Lemke et al. |

FOREIGN PATENT DOCUMENTS

| CN | 101596422 A | 12/2009 |
| JP | 2253813 A | 10/1990 |
| JP | 2258006 A | 10/1990 |
| WO | 02/02585 A2 | 1/2002 |

OTHER PUBLICATIONS

Suen, Shing-Yi, et al. "Comparison of Ligand Density and Protein Adsorption on Dye Affinity Membranes Using Difference Spacer Arms", Separation Science and Technology, 35:1 (2000), pp. 69-87.
International Search Report for PCT/SG2011/000069 mailing date of Apr. 12, 2011.

* cited by examiner

*Primary Examiner* — Chester Barry
(74) *Attorney, Agent, or Firm* — Cantor Colburn LLP

(57) ABSTRACT

A substrate having compounds disposed thereon for immobilizing a functional molecule, each compound having a chain comprising: a moiety R that is chemically coupled to the substrate, said moiety R being selected from the group consisting of an ether, ester, carbonyl, carbonate ester, thioether, disulfide, sulfinyl, sulfonyl, and carbonothioyl; and an epoxide-containing moiety that is coupled to the moiety R by a linker comprising at least one nucleophilic group. Methods of preparing the substrate and use of the substrate are also disclosed.

25 Claims, 5 Drawing Sheets

METHOD OF PREPARING A SUBSTRATE FOR IMMOBILIZATION OF FUNCTIONAL SUBSTANCES THEREON AND THE SUBSTRATE OBTAINED THEREFROM

TECHNICAL FIELD

The present invention generally relates to a substrate for immobilization of functional substances. The present invention also relates to methods of preparing the substrate.

BACKGROUND

Biological and chemical assays and processes that are used analytically or preparatively for research, clinical, diagnostic and industrial purposes often require fixation, or immobilization, of a functional substance onto a solid support (or substrate). This fixation often improves the stability and versatility of the substance without compromising its effectiveness and activity, and enables repeated usage of the substance. For example, functional substances which include biological substances such as enzymes, are typically immobilized on an inert support like silica or polyacrylamide gel to improve their stability against changing pH or temperature conditions when used in enzyme-catalyzed industrial processes, and to facilitate their subsequent separation from the reaction products. This enables re-use of the immobilized enzymes and significantly facilitates product purification, which leads to more cost-effective processes.

Immobilization of a functional substance including a biological substance may be effected by physical immobilization or chemical immobilization. One form of physical immobilization is physical adsorption (physisorption), where the functional or biological substance is attached to the substrate via encapsulation or electrostatic, hydrophobic or Van der Waals forces. Whilst physical adsorption provides a relatively simple immobilization method with wide applicability to a whole range of functional and/or biological substances, it often does not provide a sufficiently stable immobilization and is susceptible to leaching of the immobilized functional and/or biological substances.

A more stable method of immobilization of functional and/or biological substances is chemical immobilization which covalently binds the functional and/or biological substance to the substrate as a result of a chemical reaction. Chemical immobilization typically results in improved activity, reduced non-specific adsorption, and higher stability of the functional and/or biological substance. However, chemical immobilization generally requires the chemical modification of the functional and/or biological substance or the substrate to promote their efficient binding.

Modification of the surface of a solid support material or "pre-activation" of a solid support, to improve its binding to a functional and/or biological substance, typically involves the incorporation of reactive chemical moieties onto the surface of the generally poorly reactive polymeric material. Surface modification can be achieved by physical means, such as non-covalent attachment of an affinity spacer, or chemical means such as glutaraldehyde activation, cyanogen bromide activation, bromoacetylation, diazotation, ionizing-radiation induced oxidation and chemical grafting.

The non-covalent attachment of an affinity spacer is, however, associated with poor reproducibility and/or unstable binding to the surface of the substrates. Some covalent attachments, most noteworthy imines, but to a lesser extent also esters, can be hydrolyzed under the reaction conditions used for enzymatic reactions, resulting in partial loss of immobilized enzyme and leakage of enzyme into the reaction medium. Such problems may affect, amongst others, immobilization methods based on glutaraldehyde activation and bromoacetylation. Whilst diazotation, cyanogen bromide activation, ionizing-radiation induced oxidation, and chemical grafting produce covalent bonds which are more stable than non-covalent bonds, these methods involve the use of hazardous, expensive, complicated, and/or harsh reaction conditions.

Some of these methods also result in a high net charge on the solid support, which causes undesirable non-specific electrostatic binding of the functional and/or biological substance during subsequent procedures in a biological/chemical process. Another common problem encountered with the use of harsh reaction conditions is the unfavorable modification of surface properties, which may hamper the attachment of a functional and/or biological substance, particularly a large polymeric substance. This can lead to low loading of the functional and/or biological substance onto the substrate. Yet other problems encountered with some commercially available activated solid supports are low stability, pronounced toxicity and a lack of biocompatibility, resulting in short shelf life, difficult handling, and limited applicability for medical purposes.

Some of these methods rely on the further modification of "pre-activated" supports with an epoxysilane coupling agent for the immobilization of hydrophilic molecules. Other methods rely on preparation of a substrate by reacting a bisepoxy-oxirane linker to immobilize a molecule to the substrate. The aliphatic linkers used in these methods lead to a decrease in the amount of reactive groups available for immobilization, a decrease in biocompatibility and a decrease in reproducibility.

There is a need to provide methods of preparing a substrate for immobilization of functional and biological substances that overcome, or at least ameliorate, one or more of the disadvantages described above.

There is a need to provide methods that are convenient, inexpensive, robust, and reliable for preparing a substrate for immobilization of functional and biological substances.

There is also a need to provide substrates which are stable, easy to handle, inexpensive, non-toxic, biocompatible and bio-degradable for immobilization of functionally and biologically active substances and which can be used for immobilization of a wide range of substances at high loading densities with improved activity and reactivity.

SUMMARY

According to a first aspect of the invention there is provided a substrate having compounds disposed thereon for immobilizing a functional molecule, each compound having a chain comprising: a moiety R that is chemically coupled to the substrate, said moiety R being selected from the group consisting of an ether, ester, carbonyl, carbonate ester, thioether, disulfide, sulfinyl, sulfonyl, and carbonothioyl; and an epoxide-containing moiety that is coupled to the moiety R by a linker comprising at least one nucleophilic group.

In one embodiment, the substrate comprises an additional epoxide containing group coupled to the chain. In another embodiment the number of additional epoxide containing group is selected from the number 1, 2, 3, 4, and 5. In one embodiment the linker comprises additional nucleophilic groups to which said additional epoxide containing groups are coupled to said chain. This is advantageous, as the density of the epoxide-containing groups available to react with a functional molecule is increased and consequently the number of immobilization sites that are available for immobilizing a substance is also increased.

It is an advantage of the disclosure that the linker increases the length of the tether between the functional molecule and the substrate and aids in the binding of the functional molecule to the substrate.

In another embodiment the linker comprises a di-nucleophilic species. In one embodiment, the di-nucleophilic linker is selected from at least one of an alkyl-diamine and an alkene-diamine. Advantageously, the diamine linker may introduce additional sites for epoxy-activation. Without being bound by theory, it is believed that up to five molecules of epoxide-containing compound (such as epichlorohydrin) can react with one molecule of diamine linker. This is advantageous as this permits an increase in the density of, for example, an epoxide-containing compound and consequently the number of immobilization sites that are available for immobilizing a functional molecule.

In another embodiment, the linker comprises a polynucleophilic species. In another embodiment the polynucleophilic species may be a polyamine such as putrescine, spermidine, spermine, cadaverine, diethylene triamine, triethylene tetramine, tetraethylene pentamine, and tetrahydrofurfuryl amine.

The introduction of the amine groups of the linker also beneficially serves as an internal pH buffer for the immobilized substance. It is a further advantage that amine groups can also function as ion-exchangers to provide stabilizing conditions for the immobilized substance. It is a further advantage that amine groups are strongly nucleophilic making the coupling of the first and second epoxide-containing compound more efficient than other nucleophilic groups, for example OH groups. The strongly nucleophilic nature of the amine groups of the linker is further advantageous as this permits the use of long linkers whilst maintaining reactivity with the epoxide-containing compound. This is further advantageous as the use of longer linkers permits a further reduction of steric hindrance between the substrate and the immobilized substance. More advantageously, diamines such as hexanediamine are relatively cheap as compared to other linkers and are commercially available commodity materials. The low cost of hexanediamine ensures that the disclosed substrate can be mass-produced at relatively low costs.

It is a further advantage that the alkyl-amine bond formed between the epoxide-containing compound and the hexanediamine linker is resistant to hydrolysis under physiological conditions such that it can be used in aqueous systems, for example dialysis devices. It is a further advantage that the substrate in accordance with the disclosure is biologically inert.

According to a second aspect, there is provided a method of immobilizing a functional molecule on a substrate comprising the step of exposing the functional molecule to the substrate according to the disclosure.

According to a third aspect there is provided a method of preparing a substrate for immobilization of functional molecules thereon, the method comprising the steps of: (i) providing electrophilic compounds coupled to the surface of the substrate; (ii) allowing the electrophilic compounds to undergo a nucleophilic substitution reaction to provide a nucleophilic group thereon and thereby increase the nucleophilicity of the substrate surface; (iii) allowing the nucleophilic group to undergo a nucleophilic substitution reaction with another electrophilic compound to provide an electrophilic group on the substrate surface and thereby increase the electrophilicity of the substrate.

It is an advantage of the method that the elongated spacer attached to the electrophilic groups of the substrate provides increased accessibility of the functional compound to the electrophilic group and concomitantly permits an increase in the density and reactivity of the electrophilic group to the functional molecule to thereby immobilize the functional molecule on the substrate. It is a further advantage that step (iii) of the method also provides increased accessibility of a functional molecule to the electrophilic group for subsequent immobilization on the substrate.

In one embodiment, steps (ii) and (iii) are repeated n number of times to form n generations of electrophilic groups on said substrate. This is advantageous as this permits an elongation of the spacer and an increase in the density of the electrophilic groups and consequently the number of immobilization sites that are available for immobilizing a functional molecule to the substrate.

It is a further advantage that step (iii) of the method permits a relatively faster reaction between the linker and the second electrophilic compound. This results in a decreased rate of hydrolysis of the electrophilic compounds and a higher incorporation of non-hydrolysed electrophilic groups on to the substrate. This is a further advantage, as this also permits an increase in the density of the electrophilic groups on the substrate for immobilizing a functional molecule.

It is a further advantage of the method that the electrophilic groups are displaced relative to the substrate such that the ability of the functional molecule to be immobilized thereon is enhanced relative to having a substrate with only one electrophilic compound being directly coupled to a substrate. It is a further advantage that this relative displacement also permits increased accessibility of a functional molecule to the electrophilic group for subsequent immobilization on the substrate.

According to a fourth aspect, there is provided a sorbent cartridge for use in a dialysis device, the sorbent cartridge comprising a substrate as described herein for immobilizing urease.

According to a fifth aspect, there is provided a dialysis method comprising the steps of: exposing a dialysate containing urea to a substrate as described herein; and removing the dialysate from said substrate.

According to a sixth aspect, there is provided a dialyzer for use in a dialysis device, the dialyzer comprising a substrate as described herein for immobilizing urease. Hence, urease may be immobilised onto a dialysis membrane such as a cellulose acetate membrane filter comprised within the dialyser.

According to a sixth aspect, there is provided a method of modifying a dialysis membrane for immobilizing functional molecules thereon, the method comprising the steps of:
(i) coupling electrophilic compounds to the membrane surface;
(ii) allowing the electrophilic compounds to undergo a nucleophilic substitution reaction to provide a nucleophilic group thereon and thereby increase the nucleophilicity of the membrane surface; and
(iii) allowing the nucleophilic group to undergo a nucleophilic substitution reaction with another electrophilic compound to provide an electrophilic group on the membrane surface and thereby increase the electrophilicity of the membrane surface for immobilizing functional molecules thereon.

In one embodiment, the membrane is a cellulose acetate membrane.

Advantageously, the method can be used to modify an off-the-shelf dialysis membrane, such as a cellulose acetate membrane, of a dialyzer. This modification step allows the surface of the dialysis membrane to have an increased ability to immobilize functional molecules, such as dialysate enzymes, thereon when used in a dialyzer.

According to a eighth aspect, there is provided the use of the substrate as described herein in a dialysis device.

In one embodiment, there is provided a method of preparing a substrate for immobilization of functional substances thereon, the method comprising the steps of chemically coupling a first electrophilic compound to the substrate; and chemically coupling a second electrophilic compound to the first electrophilic compound that has been coupled to the substrate, wherein said second electrophilic compound, when coupled to said first electrophilic compound, is configured to immobilize the functional substance thereon.

Advantageously, the first and second electrophilic compounds are selected to be displaced relative to each other such that the ability of the functional substance to be immobilized thereon is enhanced relative to having a substrate with only one electrophilic compound being coupled to a substrate. More advantageously, the first and second electrophilic compounds are selected to be displaced relative to each other such that steric hindrance effects in the neighborhood of the second electrophile are reduced or minimized to enhance binding of the functional substance to the second electrophilic compound in use.

More advantageously, the first and/or second electrophilic compound may be a di-electrophile that effectively converts a poorly nucleophilic substrate into a strongly electrophilic substrate. This constitutes a change in polarity and reactivity of the substrate.

More advantageously, the method is a simple and cost efficient way to produce a substrate that has a relatively high reactivity to functional substances for immobilization thereon as compared to substrates produced by known methods. More advantageously, the second electrophilic compound is capable of binding stably to a functional substance including a biological substance such as an enzyme. Even more advantageously, the second electrophilic compound offers a binding site for the functional substance that is at an appropriate distance away from substrate such that steric hindrance is reduced. In one embodiment, the density of electrophilic groups per gram of the substrate is from about 0.1 to about 1 mmol/g.

This in turn reduces impediment during the immobilization of the functional substance and allows the functional substance to be anchored to the substrate easily, via the second epoxide containing compound. It also enhances the accessibility and structural flexibility of the bound substance (enzyme), thereby increasing its activity. The disclosed method is also capable of producing substrates that can immobilize chiral ligands, affinity ligands and/or ion exchange particles.

In one embodiment, the first and second electrophilic compounds are epoxide containing compounds. In one embodiment, the disclosed method comprises the step of using a linker to couple the second epoxide-containing compound to the first epoxide containing compound. This increases the length of the tether between the active oxirane site and the substrate and aids in the binding of the functional substance to the oxirane site. It also enhances the accessibility and thereby the activity of the bound substance such as an enzyme. Advantageously, the linker may contain additional functional groups to impart desirous chemical properties to the substrate. For example, the linker may contain amine groups that have buffering properties which may be beneficial when the substrate is used in applications such as dialysis devices. The linker may also contain groups that can function as anti-oxidants or metal scavengers which supplements the functions of the substrate in certain applications. More advantageously, the linker may also provide increased sites for binding of the second electrophilic compound and/or subsequent epoxide-containing compounds. In effect, the linker may increase the number of epoxide-containing compounds coupled to the substrate which in turn increases the probability and strength of immobilization of the functional substance. The linker may also be neutral and inert which does not adversely affect the functional or biological property of a functional or biological substance coupled to it.

In one embodiment, the linker does not contain an epoxide group. The functional linker may also comprise a nucleophilic group. Advantageously, the nucleophilic group is reactive and capable of chemically binding to the electrophilic (epoxide-containing) compounds. In one embodiment, the functional linker is a di-nucleophilic linker. The presence of two nucleophilic groups allows the linker to bind to both the first and second epoxide-containing compounds, forming a bridge between the two epoxide-containing compounds. In one embodiment, at least one of the nucleophiles of the di-nucleophilic linker is selected from the group consisting of NH, NR, NHO, NRO, O, S, Se, COO, CONH, CONR, CSS, COS, CONHO, CONRO, CONHNH, CONRNH, CONR$^1$NR$^2$, CNO, Ph and PR, where R, R$^1$ and R$^2$ are independently selected from the group consisting of hydrogen, optionally substituted alkyl, optionally substituted alkenyl, optionally substituted alkynyl, optionally substituted aryl and optionally substituted heteroaryl.

The di-nucleophilic linker may also have the general formula (I):

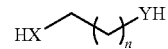

formula (I)

wherein:

X and Y are independently selected from NH, NR, NHO, NRO, O, S, Se, COO, CONH, CONR, CSS, COS, CONHO, CONRO CONHNH, CONRNH, CONRNR, CNO, PH and PR;

R is selected from the group consisting of hydrogen, optionally substituted alkyl, optionally substituted alkenyl, optionally substituted alkynyl, optionally substituted aryl and optionally substituted heteroaryl; and n is an integer from 0 to 25.

In another embodiment the di-nucleophilic linker has the general formula (II):

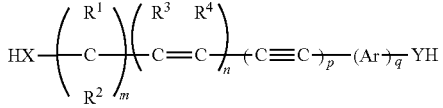

formula (II)

wherein:

X and Y are independently selected from NH, NR, NHO, NRO, O, S, Se, COO, CONH, CONR, CSS, COS, CONHO, CONRO CONHNH, CONRNH, CONRNR, CNO, PH, PR;

where R, R$^1$, R$^2$, R$^3$, R$^4$ are independently selected from the group consisting of hydrogen, optionally substituted alkyl, optionally substituted alkenyl, optionally substituted alkynyl, optionally substituted aryl and optionally substituted heteroaryl; and m, n, p and q is an integer independently selected from 0 to 25.

In one embodiment, the di-nucleophilic linker is an alkyldiamine such as hexanediamine or ethylene diamine. Advantageously, the diamine linker may introduce additional sites for epoxy-activation. Without being bound by theory, it is believed that up to five molecules of epoxide-containing compound (such as epichlorohydrin) can react with one molecule of diamine linker. This is advantageous as this permits an increase in the density of, for example, an epoxide-containing compound and consequently the number of immobilization sites that are available for immobilizing a substance. The introduction of the amine groups of the linker also beneficially serves as an internal pH buffer for the immobilized substance. It is a further advantage that amine groups can also function as ion-exchangers to provide stabilizing conditions for the immobilized substance. It is a further advantage that amine groups are strongly nucleophilic making the coupling of the first and second epoxide-containing compound more efficient than other nucleophilic groups. The strongly nucleophilic nature of the amine groups of the linker is further advantageous as this permits the use of long linkers whilst maintaining reactivity with the epoxide-containing compound. This is further advantageous as the use of longer linkers permits a further reduction of steric hindrance between the substrate and the immobilized substance. More advantageously, the hexanediamine is relatively cheap as compared to other linkers and is a commercially available commodity material. The low cost of hexanediamine ensures that the disclosed substrate can be mass-produced at relatively low costs. It is a further advantage that the alkyl amine bond formed when using a hexanediamine linker is resistant to hydrolysis under physiological conditions such that it car be used in aqueous systems, for example dialysis devices. It is a further advantage of the hexanediamine linker that it is biocompatible and biodegradable.

In one embodiment at least one of the electrophilic compound and the second electrophilic compound is an epihalohydrin. Preferably, the epihalohydrin is epichlorohydrin. Similarly, epichlorohydrin is relatively cheap as compared to other epihalohydrins and is procurable easily as it is a commercially available commodity material. Again, the low cost of epichlorohydrin ensures that the disclosed substrate can be mass-produced at relatively low costs. Epichlorohydrin also tends to react very rapidly and exhaustively, only giving non-toxic products (glycerol and amino-glycerols) and thus is suitable for use in preparing a substrate that would eventually be used for medical applications. Moreover, because epichlorohydrin is partly miscible with water and fully miscible with alcohol any excess epichlorohydrin can be relatively easily removed by washing the substrate with water and/or alcohol. Furthermore, epichlorohydrin and its hydrolysis products are volatile and can therefore be efficiently removed by evaporation.

In one embodiment, the method comprises selecting a poorly reactive substrate. The substrate of the disclosed method may be a bead, micro-sized particle, nanosized particle, a membrane, a mesh, a scaffold or any solid support that is capable of being prepared using the disclosed method to immobilize a functional substance including a biological substance thereon. In one embodiment, the substrate is selected from the group consisting of a polyester substrate, a polyamide substrate, an epoxy resin substrate, a polyacrylate substrate, a hydroxyl-functionalized substrate and a polysaccharide-based substrate. The polysaccharide-based substrate may be selected from the group consisting of cotton linters, cotton pulp, cotton fabrics, cellulose fibers, cellulose beads, cellulose powder, microcrystalline cellulose, cellulose membranes, rayon, cellophane, cellulose acetate, cellulose acetate membranes, chitosan, chitin, dextran derivatives and agarose derivatives. The substrates may also be biodegradable and thus environmentally friendly, which allows their application in environmentally sensitive applications such as agricultural applications or waste treatment applications. The substrate may also be biocompatible such that when the substrate is implanted into the human body or in conjunction with the human body, for example in dialysis, little or no adverse health effects are elicited.

The chemical coupling steps of the disclosed methods may be undertaken at a temperature range of from $-30°$ C. to $100°$ C., preferably from $0°$ C. to $100°$ C. In one embodiment, the step of chemically coupling a first electrophilic compound to the substrate is carried out at a temperature from about $50°$ C. to $60°$ C.; the step of chemically coupling a linker to the first electrophilic compound is carried out at a temperature from about $20°$ C. to $40°$ C.; the step of chemically coupling a second electrophilic compound to the linker is carried out at a temperature from about 20 to $40°$ C.; and the step of chemically coupling the functional substance to the second electrophilic compound is carried out at a temperature from about 2 to $6°$ C. Advantageously, the substrate can be produced and/or prepared at mild conditions for example at room temperature, and in normal atmosphere. This again translates to lower production costs and increased ease of handling. More advantageously, the final immobilization reaction can be carried out under very mild conditions, such as in aqueous buffer at 2 to $6°$ C. and normal atmosphere, and does not require any additional reagents. This eliminates the risk of deactivation or denaturation of the bioactive substance by extreme conditions or strong reagents, such as might be problematic in other immobilization methods. Even more advantageously, as the method can be carried out at ambient temperatures, the immobilization of bioactive substances on the substrate might also be carried out simultaneously or subsequent to the activation of the substrate.

In one embodiment, the functional substances are biologically active substances such as enzymes, for example urease. Advantageously, when urease is immobilized on the substrate, the substrate containing the immobilized urease can be used for dialysis applications, for example for the regeneration of peritoneal dialysate or hemodialysate. The enzymes may also be at least one of uricase, creatininase, lipase, esterase, cellulase, amylase, pectinase, catalase, acylase, penicillin amidase, proteinase-K.

In one embodiment, the disclosed method further comprises the step of chemically coupling one or more subsequent electrophilic compounds to both the first and second electrophilic compounds, wherein said subsequent electrophilic compound(s), when coupled to both said first and second electrophilic compounds is/are configured to immobilize the functional substance thereon. For example, a third, fourth, fifth, sixth electrophilic compound and so on may be coupled to both the first and second electrophilic compounds. The electrophilic groups as disclosed herein may contain at least one epoxide group.

In another embodiment, there is provided a method of immobilizing a functional molecule on a substrate, the method comprising the steps of providing the substrate having compounds thereon prepared by the method of the disclosure, each of said compounds comprising an ether-containing moiety that is chemically coupled to the substrate and an epoxide-containing moiety that is coupled to the ether moiety; and introducing a solution containing said functional molecule to said compounds disposed on said substrate wherein the epoxide-containing moiety forms a chemical bond with said functional molecule to immobilize it thereto.

Advantageously, this chemical bond may be a non-hydrolyzable covalent bond, such as an amine-bond. Consequently, the functional molecule will be immobilized on the substrate with sufficient stability and cannot be easily removed from the substrate.

The method of the second aspect may further comprise the step of applying a substantially homogenous mixture of stabilizing additives onto the surface of the substrate to stabilize said functional molecule. In one embodiment, the step of applying the substantially homogenous mixture of additives comprises evaporating the solvent of a solution of said additives onto the substrate. The stabilizing additives may be selected from the group consisting of a sugar such as glucose, an organic acid such as ethylenediaminetetraacetic acid, an amino acid such as cysteine and a sugar acid such as ascorbic acid and thiols such as mercaptoethanol.

In another embodiment, there is provided a substrate having compounds disposed thereon for immobilizing a functional molecule, each compound comprising an ether-containing moiety that is chemically coupled to the substrate and an epoxide-containing moiety that is coupled to the ether moiety by a linker comprising at least one nucleophilic group whereby said epoxide-containing moiety is disposed from said ether-containing moiety to immobilize the functional molecule to said epoxide-containing moiety without substantial steric hindrance being caused by said ether containing moiety or the substrate. Advantageously, the substrate has an improved stability and can be produced at a relatively low cost when compared to known substrates that can effectively immobilize functional substances. More advantageously, the substrate can be reused repeatedly without substantially losing its enzymatic properties, due to the high stability of bonding between the biomolecule and the epoxide-containing moiety. In addition, as there is no leaching of potentially hazardous substances the substrate is suitable for use in medical applications such as for peritoneal dialysis.

In one embodiment, the linker is a non-hydrocarbon such as hydrazine, hydroxylamine, ammonia, water, or hydrogen sulfide.

In one embodiment, the linker is a saturated or unsaturated aliphatic chain having from 2 to 18 carbon atoms, 2 to 16 carbon atoms, 2 to 14 carbon atoms, 2 to 12 carbon atoms, or 2 to 10 carbon atoms, 2 to 8 carbon atoms, 2 to 6 carbon atoms, and 2 to 4 carbon atoms. In one embodiment, the linker is a saturated aliphatic chain having 4 to 8 carbon atoms, more preferably 6 carbon atoms. The nucleophilic group of said linker may be located at one of the terminal ends of the aliphatic chain or in between the terminal ends of the aliphatic chain. In one embodiment the nucleophilic group of said linker may be chemically coupled to the aliphatic chain by way of a branch chain extending therefrom. In one embodiment, there are two nucleophilic groups disposed on said linker, preferably at terminal ends of the aliphatic chain. In one embodiment at least one nucleophilic group is disposed on a terminal end of the aliphatic chain and is coupled to either the ether or epoxide-containing moiety with a secondary aliphatic linker chain therebetween. The secondary aliphatic linker chain may have from 1 to 3 carbon atoms.

The substrate may further comprise a coating disposed on said substrate, the coating comprising a substantially homogenous mixture of stabilizing additives. The stabilizing additives may be selected from the group consisting of a sugar such as glucose an organic acid such as ethylenediaminetetraacetic acid, an amino acid such as cysteine and a sugar acid such as ascorbic acid.

In another embodiment there is provided a sorbent cartridge for use in a dialysis device the sorbent cartridge comprising a substrate having compounds disposed thereon that comprise an immobilized urease, each compound comprising an ether-containing moiety that is chemically coupled to the substrate and an epoxide-containing moiety that is coupled to the ether moiety by a linker comprising at least one nucleophilic group whereby said epoxide-containing moiety is disposed from said ether-containing moiety to immobilize the urease molecule to said substrate without substantial steric hindrance being caused by said ether containing moiety or the substrate.

In another embodiment there is provided a dialysis method comprising the steps of exposing a dialysate containing urea to a substrate having compounds disposed thereon that comprise an immobilized urease, each compound comprising an ether-containing moiety that is chemically coupled to the substrate and an epoxide-containing moiety that is coupled to the ether moiety by a linker comprising at least one nucleophilic group whereby said epoxide-containing moiety is disposed from said ether-containing moiety to immobilize the urease molecule to said substrate without substantial steric hindrance being caused by said ether containing moiety or the substrate; and removing the dialysate from said substrate after at least a portion of said urea has been broken down.

In another embodiment, there is provided the use of the substrate according to the disclosure in a dialysis device. Advantageously, the substrate can be used to remove toxins from the dialysate in the dialysis device effectively and safely.

DEFINITIONS

The following words and terms used herein shall have the meaning indicated:

The term "epoxide", "epoxy group" or "oxirane" depicts a chemical functional group consisting of a three-membered ring arrangement of two carbon atoms and one oxygen atom. The two carbon atoms in the three-membered ring may be independently substituted. The term "epoxide" may also depict a molecule or compound that comprises at least one epoxy group.

The term "epoxide-containing compound" means any compound that is an epoxide or a compound which contains an epoxide moiety. Exemplary epoxide containing compounds are alkylene oxides and in particular lower alkylene oxides such as ethylene oxide, propylene oxide, butylene oxide, alcohol epoxides such as glycidol, and epihalohydrins such as epichlorohydrin, epibromohydrin, epiiodohydrin, 1,2-epoxy-4-chlorobutane, 1,2-epoxy-4-bromobutane, 1,2-epoxy-4-iodobutane, 2,3-epoxy-4-chlorobutane, 2,3-epoxy-4-bromobutane, 2,3-epoxy-4-iodobutane, 2,3-epoxy-5-chloropentane, 2,3-epoxy-5-bromopentane, 1,2-epoxy-5-chloropentane, etc., epoxy compounds such as 2,2-bis(p-1,2-epoxypropoxyphenyl)-propane, 1,4-bis(1,2-epoxypropoxy)benzene, N,N'-bis(2,3-epoxypropyl)piperazine, etc.

The terms "electrophilic group", "electrophile" and the like as used herein refers to an atom or group of atoms that can accept an electron pair to form a covalent bond. The "electrophilic group" used herein includes but is not limited to halide, carbonyl and epoxide containing compounds. Common electrophiles may be halides such as thiophosgene, glycerin dichlorohydrin, phthaloyl chloride, succinyl chloride, chloroacetyl chloride, chlorosuccinyl chloride, etc.; ketones such as chloroacetone, bromoacetone, etc.; aldehydes such as glyoxal, etc.; isocyanates such as hexamethylene diisocyanate, tolylene diisocyanate, meta-xylylene diisocyanate, cyclohexylmethane-4,4-diisocyanate, etc and derivatives of these compounds.

The terms "nucleophilic group", "nucleophile" and the like as used herein refers to an atom or group of atoms that have an electron pair capable of forming a covalent bond. Groups of this type may be ionizable groups that react as anionic groups. The "nucleophilic group" used herein includes but is not limited to hydroxyl, primary amines, secondary amines, tertiary amines and thiols.

The term "ether" or "ether containing" refers to a class of organic compounds of general formula R—O—R, wherein R is carbon. The term "ether" or "ether containing" as used herein is intended to exclude those compounds where R is not carbon for example sialyl ethers, Si—O—Si.

The term "polyamine" refers to an organic compound having at least two positively amino groups selected from the group comprising primary amino groups secondary amino groups and tertiary amino groups. Accordingly, a polyamine covers diamines, triamines and higher amines.

The term "biodegradable" or "biodegradable polymer" as used herein refers to environmentally-friendly materials that are degradable and/or compostable. Such materials may be degradable/compostable by various living organisms or by exposure to light and/or oxygen. Therefore, the term "biodegradable", as used herein will be understood to include materials that are oxobiodegradable, photobiodegradable and microbially biodegradable.

The term "biocompatible" or "biocompatible polymer" refers to polymers which, in the amounts employed, are non-toxic, non-migratory, chemically inert, and substantially non-immunogenic when used in contact with biological fluids, for example plasma or blood. Suitable biocompatible polymers include, by way of example, polysaccharides such as cellulose or chitin.

The term "biopolymer" refers to polymers that are produced by or derived from living organisms. Exemplary biopolymers include polypeptides, nucleic acids and polysaccharides, for example cellulose and chitin.

The term "functional", when used to describe a molecule or substance, refers to a group of atoms arranged in a way that determines the chemical properties of the substance and the molecule to which it is attached. Examples of functional groups include halogen atoms, amide groups, hydroxyl groups, carboxylic acid groups and the like.

The term "target molecule" refers to a molecule that is to be detected, isolated, or tested for, and that is capable of reacting with or binding to a functional substance such as a biological substance. Exemplary target molecules include proteins, polysaccharides, glycoproteins, hormones, receptors, lipids, small molecules, drugs, metabolites, cofactors, transition state analogues and toxins, or any nucleic acid that is not complementary to its cognate nucleic acid. The target molecule may be in vivo, in vitro, in situ, or ex vivo.

The term "functional substances" and the like, used herein refers broadly to mean molecules or active substances having a site capable of reacting with or bonding with or having ah affinity with a target molecule. The term "functional substances" and the like broadly encompasses the biological substances and biomolecules.

The terms "biological substances" or "biomolecules" and the like, used herein, refer to any substances and compounds substantially of biological origin. Hence, the terms encompass hot only native molecules, such as those that can be isolated from natural sources, but also forms, fragments and derivatives derived therefrom as well as recombinant forms and artificial molecules, as long as at least one property of the native molecules is present. Hence, the term covers organic molecules that are produced by a living organism, including large polymeric molecules such as proteins, polysaccharides and nucleic acids as well as small molecules such as primary metabolites, secondary metabolites and natural products.

The terms "biologically active substances", "bioactive substances" and the like, used herein, refer broadly to mean biological molecules or physiologically active substances having a site capable of reacting with or bonding with or having an affinity with a target molecule. This includes but is not limited to substances having a catalytically active site such as enzymes, substances having a site capable of bonding to specific compounds or specific classes of compounds, such as nucleic acids oligonucleotides, deoxyribonucleic acid (DNA), ribonucleic acid (RNA), or lectins, vitamins, peptides, proteins, hormones, endocrine disturbing chemicals, sugars, lipids and the like.

The term "poorly reactive substrate" means a substrate that is composed of a material that does not appreciably react chemically or biologically with a functional or biological substance as defined above. In some embodiments, the functional of biological substance may comprise a biomolecule and the non-reactive substrate is composed of a material that is bio-compatible in that the substrate material is not toxic and does not cause any adverse health effect to the human body. Non-reactive substrates that are also biocompatible are typically polymeric materials that are generally insoluble, flexible and which can conform to many different shapes, including curved surfaces. It is noted that the term "polymer" is used to denote a chemical compound with high molecular weight consisting of a number of structural units linked together by covalent bonds. One exemplary polymeric material that is non-reactive and biocompatible with biological substances as defined above is the polysaccharide cellulose.

The terms "linker" and "spacer" as used herein refer to an organic moiety that connects two parts of a compound.

As used herein, the term "alkyl" includes within its meaning monovalent ("alkyl") and divalent ("alkylene") straight chain or branched chain or cyclic saturated aliphatic groups having from 1 to 25 carbon atoms, eg, 1, 2, 3, 4, 5, 6, 7, 8, 9, 10, 11, 12, 13, 14, 15, 16, 17, 18, 19, 20, 21, 22, 23, 24 or 25 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like. Lower alkyls are alkyl groups as defined above 1 to 6 carbon atoms, preferably 1 to 4 carbon atoms.

The term "alkenyl" as used herein includes within its meaning monovalent ("alkenyl") and divalent ("alkenylene") straight or branched chain or cyclic unsaturated aliphatic hydrocarbon groups having from 2 to 25 carbon atoms, eg, 2, 3, 4, 5, 6, 7, 8, 9, 10, 11, 12, 13, 14, 15, 16, 17, 18, 19, 20, 21, 22, 23, 24 or 25 carbon atoms and having at least one double bond, of either E, Z, cis or trans stereochemistry where applicable, anywhere in the alkyl chain. Examples of alkenyl groups include but are not limited to vinyl, allyl, 1-methylvinyl, 1-propenyl, 2-methyl-1-propenyl, 2-methyl-1-propenyl, 1-butenyl, 2-butenyl, 3-butenyl, 1,3-butadienyl, 1-pehtenyl, 2-pentenyl, 3-pentenyl, 4-pentenyl, 1,3-pentadienyl, 2,4- pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, 1-nonenyl, 1-decenyl, and the like. Lower alkenyls are alkenyl groups as defined above with 2 to 6 carbon atoms preferably 2 to 4 carbon atoms.

The term "alkynyl" as used herein includes within its meaning monovalent ("alkynyl") and divalent ("alkynylene") straight or branched chain or cyclic unsaturated aliphatic hydrocarbon groups having from 2 to 10 carbon atoms and having at least one triple bond anywhere in the carbon chain. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, methylpentynyl, 1-heptynyl, 2-heptynyl, 1-octynyl, 2-octynyl, 1-nonyl, 1-decynyl, and the like. Lower alkynylene are alkynylene groups as defined above with 2 to 6 carbon atoms, preferably 2 to 4 carbon atoms.

The term "aryl" as used herein refers to a mono- or multiple-cyclic carbocyclic ring system having one or more aromatic rings including, but not limited to, phenyl, naphthyl, tetrahydronaphthyl, indanyl, indenyl and the like. Aryl groups (including bicyclic aryl groups) can be unsubstituted or substituted with one to five substituents or more (typically one to five substituent for monocyclic aryl and more than five substituents for bicyclic/oligocylic aryl) independently selected from the group consisting of alkyl, alkenyl, alkynyl, haloalkyl, alkoxy, thioalkoxy, hydroxy, mercapto, amino, alkylamino, dialkylamino, acylamino, aminoacyl, alkoxycarbonyl, aryloxycarbonyl, azido, cyano, halo, nitro, carboxaldehyde, carboxy, carboxamide, carbamide, carbamate, sulfate, sulfonate, sulfinate, phosphate, phosphonate, phosphinate, phosphine, and protected hydroxy. In addition, substituted aryl groups include tetrafluorophenyl and pentafluorophenyl.

The term "heteroaryl", whether used alone or as part of another group, refers to a substituted or unsubstituted aromatic heterocyclic ring system (monocyclic or bicyclic). Heteroaryl groups can have, for example, from about 3 to about 50 carbon atoms. Heteroaryl groups typically include aromatic heterocyclic rings systems having about 4 to about 14 ring atoms and containing carbon atoms and 1, 2, 3, or 4 heteroatoms selected from oxygen, nitrogen or sulfur. Exemplary heteroaryl groups include but are not limited to furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. The term "heteroaryl" also includes aromatic heterocyclic rings that are substituted, for example with 1 to 5 substituents independently selected from the group consisting of alkyl, alkenyl, alkynyl, haloalkyl, alkoxy, thioalkoxy, hydroxy, mercapto, amino, alkylamino, dialkylamino, acylamino, aminoacyl, alkoxycarbonyl, aryloxycarbonyl, azido, cyano, halo, nitro, carboxaldehyde, carboxy, carboxamide, carbamide, carbamate, sulfate, sulfonate, sulfinate, phosphate, phosphonate, phosphinate, phosphine, and protected hydroxy.

The term "optionally substituted" as used herein means the group to which this term refers may be unsubstituted or may be substituted with one or more groups independently selected from alkyl, alkenyl, alkynyl, aryl, heteroaryl, thioalkyl, cycloalkyl, cycloalkenyl, heterocycloalkyl, halo, carboxyl, carboxyalkyl, haloalkyl, haloalkynyl, hydroxy, alkoxy, thioalkoxy, mercapto, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, aminoacyl, acyloxy, alkylsulfonyloxy, heterocycloxy, heterocycloamino, haloheterocycloalkyl, alkoxycarbonyl, aryloxycarbonyl, azido, carboxaldehyde, carboxy, carboxamide, carbamide, carbamate, oxime, hydroxylamine, sulfate, sulfonate, sulfinate, alkylsulfenyl, alkylcarbonyloxy, alkylthio, acylthio, phosphorus-containing groups such as phosphate, phosphonate, phosphinate and phosphine, aryl, heteroaryl, alkylaryl, alkylheteroaryl, cyano, cyanate, isocyanate, C(O)NH(alkyl), —C(O)N(alkyl)$_2$ and —C(O)NR'R" where R' and R" are independently hydrogen, alkyl aryl or heteroaryl as defined herein.

The term "halogen" or variants such as "halide" or "halo" as used herein refers to fluorine, chlorine, bromine and iodine. The term "amino" or "amine" as used herein refers to groups of the form —NR$_a$R$_b$ wherein R$_a$ and R$_b$ are individually selected from the group including but not limited to hydrogen, optionally substituted alkyl, optionally substituted alkenyl, optionally substituted alkynyl, and optionally substituted aryl groups.

The terms "chemically coupled" and "Chemically couple" and grammatical variations thereof refer to the covalent and noncovalent bonding of molecules and include specifically, but not exclusively, covalent bonding, electrostatic bonding, hydrogen bonding and van der Waals' bonding. The terms encompass both indirect and direct/bonding of molecules. Thus, if a first compound is chemically coupled to a second compound, that connection may be through a direct chemical bond, or through an indirect chemical bond via other compounds, linkers or connections.

As used herein, the term "urease unit", or urease "enzymatic unit", [U], refers to that amount of enzyme (urease) which causes the liberation of one micromole of ammonia per minute at 23° C. and pH 7.5.

The word "substantially" does not exclude "completely" e.g. a composition which is "substantially free" from Y may be completely free from Y. Where necessary, the word "substantially" may be omitted from the definition of the invention.

Unless specified otherwise the terms "comprising" and "comprise", and grammatical variants thereof are intended to represent "open" or "inclusive" language such that they include recited elements but also permit inclusion of additional, unrecited elements.

As used herein the term "about", in the context of concentrations of components of the formulations, typically means +/− 5% of the stated value more typically +/− 4% of the stated value, more typically +/− 3% of the stated value, more typically +/− 2% of the stated value, even more typically −/− 1% of the stated value, and even more typically +/− 05% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range for example 1, 2, 3, 4, 5, and 6. This applies regardless of the breadth of the range.

DETAILED DISCLOSURE OF EMBODIMENTS

Exemplary, non-limiting embodiments of a method of preparing a substrate for immobilization of functional substances thereon and a substrate for immobilization of functional molecules thereon will now be disclosed.

The substrate has compounds disposed thereon for immobilizing a functional molecule each compound having a chain comprising: a moiety R that is chemically coupled to the substrate, said moiety R being selected from the group consisting of an ether, ester, carbonyl, carbonate ester, thioether, disulfide, sulfinyl, sulfonyl, and carbonothioyl; and an epoxide-containing moiety that is coupled to the moiety R by a linker comprising at least one nucleophilic group.

In one embodiment, the moiety R is further selected from the group consisting of an amine, amide, carbamide, ureas and guanidines.

In one embodiment, the nucleophilic group excludes at least one of oxygen-containing moieties and sulfur-containing moieties.

In another embodiment, the substrate comprises an additional epoxide containing group coupled to the chain. In one embodiment, the number of additional epoxide containing group is selected from the number 1, 2, 3, 4 and 5. In another embodiment at least one of the additional epoxide containing groups is coupled to said chain by the nucleophilic group of said linker.

The linker may comprise additional nucleophilic groups to which said additional epoxide containing groups are coupled to said chain. In another embodiment, the additional epoxide-containing groups may branch from the chain by coupling with the additional nucleophilic groups of said linker.

In one embodiment, the nucleophilic group of said linker is an amine. The linker may be selected from the group consisting of saturated and unsaturated aliphatic and aromatic amines diamines and triamines. In one embodiment the aliphatic groups of said amines are alkyl groups.

In another embodiment, the linker may contain an epoxide group.

In another embodiment, the linker comprises a di-nucleophilic species. The di-nucleophilic linker may be selected from at least one of an alkyl-diamine and an alkene-diamine. In one embodiment, the di-nucleophilic linker is selected from at least one of ethane-diamine, propane-diamine, butane-diamine, pentane-diamine, hexane-diamine. In one embodiment, the di-nucleophilic linker is hexane-diamine.

In another embodiment, the epoxide containing-compound is derived by reaction of an epihalohydrin with the nucleophilic groups of said linker.

In one embodiment, the substrate may be inert to a functional molecule being immobilized by said epoxide-containing group.

In another embodiment, the substrate may be a polymer. The polymer may be a biocompatible polymer. In another embodiment, the biocompatible polymer may be selected from the group consisting of a polyester substrate, a polyamide substrate, a polyacrylate substrate, and a polysaccharide-based substrate. In one embodiment, the polymer is a polysaccharide-based substrate which may be selected from the group consisting of cotton linters, cotton pulp, cotton fabrics, cellulose fibers, cellulose beads, cellulose powder, microcrystalline cellulose, cellulose membranes, rayon, cellophane, cellulose acetate, cellulose acetate membranes, chitosan, chitin, dextran derivatives and agarose derivatives.

In another embodiment, the polymer is a biopolymer. The biopolymer may be selected from cellulose, chitosan, chitin, dextran, agarose and derivatives thereof.

In another embodiment, the substrate may comprise a coating disposed on said substrate, the coating comprising a substantially homogenous mixture of stabilizing additives selected to stabilize said functional molecule. In one embodiment, the stabilizing additives may be selected from the group consisting of a sugar, an organic acid, an amino acid, a sugar acid and a thiol.

In another embodiment, there is provided a method of immobilizing a functional molecule on a substrate. The method comprises the step of exposing the functional molecule to the substrate as described herein.

In one embodiment the functional molecule is selected from a group consisting of an affinity ligand, a chelator, a catalyst, an ion exchanger, a dye, an indicator and a biomolecule. In another embodiment, the functional molecule is chiral. In another embodiment, the functional molecule is a biomolecule. The biomolecule may be an enzyme. The enzyme may be selected from the group consisting of urease, uricase, creatininase, lipases, esterases, cellulases, amylases, pectinases, catalases, acylase, catalase, esterase, penicillin amidase, proteinase-K.

In another embodiment, the method further comprises the step of applying a substantially homogenous mixture of stabilizing additives to the surface of the substrate to stabilize selected to stabilize said functional molecule. The step of applying the substantially homogenous mixture of additives comprises evaporating the solvent of a solution of said additives onto the substrate. In one embodiment, the stabilizing additives are selected from the group consisting of a sugar, an organic acid, an amino acid, a sugar acid and a thiol.

In another embodiment, there is also provided a method of preparing a substrate for immobilization of functional molecules thereon. The method comprises the steps of: (i) providing electrophilic compounds coupled to the surface of the substrate; (ii) allowing the electrophilic compounds to undergo a nucleophilic substitution reaction to provide a nucleophilic group thereon and thereby increase the nucleophilicity of the substrate surface; (iii) allowing the nucleophilic group to undergo a nucleophilic substitution reaction with another electrophilic compound to provide an electrophilic group on the substrate surface and thereby increase the electrophilicity of the substrate.

In one embodiment, the steps (ii) and (iii) may be repeated n number of times to form n generations of electrophilic groups on said substrate. In one embodiment, steps (ii) and (iii) are repeated 1, 2, 3, 4, 5, 6, 7, 8, 9, 10, 11, 12, 13, 14, 15, 16, 17, 18, 19 or 20 or more times.

In one embodiment, said step of providing electrophilic compounds coupled to the surface of the substrate comprises chemically coupling a first electrophilic compound to the substrate.

In another embodiment, step (ii) comprises the step of reacting a nucleophile with the first electrophilic compound. In another embodiment, step (iii) comprises chemically coupling a second electrophilic compound to the nucleophile.

The electrophilic compound may be an epoxide-containing compound. In one embodiment, the electrophilic compound may be selected from epoxy compounds such as alkylene oxides, alcohol epoxides, and epihalohydrins, halides. The electrophilic compound may also include ketones, aldehydes, isocyanates and derivatives of these compounds.

In another embodiment, the epoxide-containing compound is an epihalohydrin. In one embodiment, the epihalohydrin may be selected from the group consisting of epichlorohydrin, epibromohydrin, epiiodohydrin, 1,2-epoxy-4-chlorobutane, 1,2-epoxy-4-bromobutane, 1,2-epoxy-4-iodobutane, 2,3-epoxy-4-chlorobutane, 2,3-epoxy-4-bromobutane, 2,3-epoxy-4-iodobutane, 2,3-epoxy-5-chloropentane, 2,3-epoxy-5-bromopentane, 1,2-epoxy-5-chloropentane.

In one embodiment, the epihalohydrin is epichlorohydrin.

In one embodiment, the nucleophile is a di-nucleophile or a polynucleophile. In another embodiment, the nucleophile comprises an amine. The amine may be selected from the group consisting of saturated and unsaturated aliphatic or aromatic amines, diamines, triamines and higher polyamines. In one embodiment, the aliphatic group of said amines is selected from an alkyl group. In one embodiment, the amine may be selected from at least one of ethane-diamine, proanediamine, butane-diamine, pentane-diamine, hexane-diamine. In one embodiment, the amine is hexane-diamine.

The substrate may comprise a polymer. The polymer may be a biocompatible polymer. In one embodiment, the biocompatible polymer may be selected from the group consisting of a polyester substrate, a polyamide substrate, a polyacrylate substrate, and a polysaccharide-based substrate.

In one embodiment, the substrate is a polysaccharide-based substrate. The polysaccharide-based substrate may selected from the group consisting of cotton linters, cotton pulp, cotton fabrics, cellulose fibers, cellulose beads, cellulose powder, microcrystalline cellulose, cellulose membranes, rayon, cellophane, cellulose acetate, cellulose acetate membranes, chitosan, chitin, dextran derivatives and agarose derivatives.

In another embodiment, the polymer may be a biopolymer. The biopolymer may be selected from cellulose, chitosan, chitin, dextran, agarose and derivatives thereof.

In another embodiment, the functional molecule may be selected from the group consisting of an affinity ligand, a chelator, a catalyst, an ion exchanger, a dye, an indicator and a biomolecule. In one embodiment, the functional molecule may be chiral. In another embodiment the functional molecule is a biomolecule. The biomolecule maybe an enzyme selected from the group consisting of urease, uricase, creatininase, lipases, esterases, cellulases, amylases, pectinases, catalases, acylase, catalase, esterase, penicillin amidase, proteinase-K.

In another embodiment, the method may further comprise the step of applying a substantially homogenous mixture of stabilizing additives to the surface of the substrate wherein said stabilizing additives are selected to stabilize said functional molecule. The step of applying the substantially homogenous mixture of additives may comprise evaporating the solvent of a solution of said additives onto the substrate. In one embodiment the stabilizing additives may be selected from the group consisting of a sugar, an organic acid, an amino acid, a sugar acid and a thiol.

There is also provided a sorbent cartridge for use in a dialysis device, the sorbent cartridge comprising a substrate as described herein for immobilizing urease.

There is also provided a dialyzer for use in a dialysis device, the dialyzer comprising a substrate as described herein for immobilizing urease.

There is also provided a dialysis method comprising the steps of: exposing a dialysate/containing urea to a substrate as described herein; and removing the dialysate from said substrate.

There is also provided the use of the substrate as described herein in a dialysis device.

In another embodiment there is provided the use of the substrate in accordance with the disclosure as a solid phase material for chromatography (including chiral chromatography and affinity chromatography). In another embodiment, the disclosure provides the use of the substrate in sensors and biosensors.

In another embodiment there is provided a method of preparing a substrate for immobilization of functional substances thereon, the method comprising the steps of chemically coupling a first electrophilic compound to the substrate; and chemically coupling a second electrophilic compound to the first electrophilic compound that has been coupled to the substrate, wherein said second electrophilic compound, when coupled to said first electrophilic compound, is configured to immobilize the functional substance thereon. In one embodiment, the first electrophilic compound is a di-electrophile and is chemically bonded to the substrate due to a nucleophilic substitution reaction between one electrophilic group of the di-electrophile and a nucleophilic group on the substrate.

As a result of this first reaction, a poorly reactive (nucleophilic) substrate is converted into a strongly reactive (electrophilic) substrate. The di-electrophilic reagent may be an epihalohydrin. It may also be one of the group comprising cyanogen bromide, bromoacetic acid, glutaric aldehyde, and the like. The second electrophilic compound may be chemically directly bonded to the first electrophilic compound such as via a chemical link. The second electrophilic compound may also be indirectly chemically, bonded to the first electrophilic compound, for example via a linker. In one embodiment, the first and second electrophilic compounds are monomers.

Prior to the step of chemically coupling a first electrophilic compound to the substrate, the method may include the step of functionalizing the substrate such that the substrate comprises functional groups that are capable of being chemically coupled to the first electrophilic compound.

In one embodiment, the method comprises the step of using a linker to couple the second electrophilic compound to the first electrophilic compound. The linker may also be neutrally charged. In one embodiment, the linker may also comprise an aliphatic $C_{1-25}$ chain that is saturated or unsaturated, straight or branched, which is optionally substituted, and wherein the carbons of the chain can be optionally replaced by —C(O)—, —C(O)C(O)—, —C(O)NR*—, —C(O)NR*NR*—, —CO$_2$—, —OC(O)—, —NR*CO$_2$—, —O—, —NR*C(O)NR*—, —OC(O)NR*—, —NR*NR*—, —NR*C(O)—, —S—, —SO—, —SO$_2$—, —NR*—, —SO$_2$NR*—, —NR*SO$_2$—, —C(O)NRO— or —NRC(NR)NR— wherein R* is selected from hydrogen or $C_{1-10}$ aliphatic; wherein $C_{1-10}$ aliphatic can be substituted or unsubstituted.

In one embodiment, the linker does not contain an epoxide group. The linker may also comprise at least one nucleophilic group. The linker may be a multi-nucleophilic linker, that is, the linker may contain more than one nucleophilic group. In one embodiment, the linker is a di-nucleophilic linker. When the linker is a di-nucleophilic linker, at least one of the nucleophiles of the di-nucleophilic linker may be selected from the group consisting of NH, NR, NHO, NRO, O, S, Se, COO, CONH, CONR, CSS, COS, CONHO, CONRO, CONHNH, CONRNH, CONRN$^1$R$^2$, CNO, PH and PR, where R, $R^1$ and $R^2$ are independently selected from the group consisting of hydrogen, optionally substituted alkyl, optionally substituted alkenyl, optionally substituted alkynyl, optionally substituted aryl and optionally substituted heteroaryl.

When the functional linker does not contain an epoxide group and is a di-nucleophilic linker, the linker may have a general formula (I):

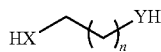

formula (I)

wherein:

X and Y are independently selected from NH, NR, O, S, COO, CONH and CONR;

R is selected from the group consisting of hydrogen optionally substituted alkyl, optionally substituted alkenyl, optionally substituted alkynyl, optionally substituted aryl and optionally substituted heteroaryl; and n is an integer from 0 to 25.

In another embodiment, the di-nucleophilic linker has the general formula (II):

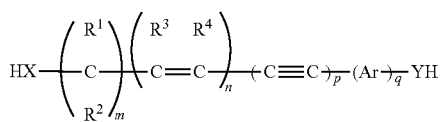

formula (II)

wherein

X and Y are independently selected from NH, NR, NHO, NRO, O, S, Se, COO, CONH, CONR, CSS, COS, CONHO, CONRO CONHNH, CONRNH, CONRNR, CNO, PH, PR;

R, $R^1$, $R^2$, $R^3$, $R^4$ are independently selected from the group consisting of hydrogen optionally substituted alkyl, optionally substituted alkenyl, optionally substituted alkynyl, optionally substituted aryl and optionally substituted heteroaryl; and m, n, p and q is an integer independently selected from 0 to 25.

The position of the groups

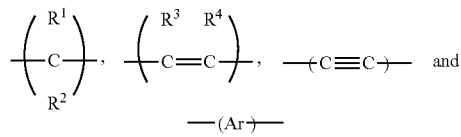

of formula (II) may be interchanged and these groups may also be present in more than one positions as will be understood by a skilled artisan.

In another embodiment the di-nucleophilic linker has the general formula (IIa):

formula (IIa)

wherein:

X and Y are independently selected from the group consisting of $NR^1R^2$, NRO, OR, SR, SeR, COOR, CONR, CSSR, COSR, CONRO, $CONRNR^1R^2$, CNOR and $PR^1R^2$, and any other substituents which may form cationic adducts;

R, $R^1$ and $R^2$ are independently selected from the group consisting of hydrogen, optionally substituted alkyl, optionally substituted alkenyl, optionally substituted alkynyl, optionally substituted aryl and optionally substituted heteroaryl; and n is an integer from 0 to 25.

In one embodiment, the variables X and Y may also be any nucleophilic group that is capable of reacting with an epoxide group to form a chemical bond.

The dinucleophilic linker may comprise an alky-diamine group. In one embodiment, the di-nucleophilic linker is at least one of ethylene-diamine and hexanediamine. In another embodiment, the linker may be a charged compound comprising nucleophiles such as $NR^1R^2$ where, $R^1$ and $R^2$ are defined above. The linker may also be small compounds selected from the group consisting of $H_2O$, $H_2S$, $H_2Se$, $PH_3$, $PH_2R$, $NH_3$, $NH_2R$ and $NHR^1R^2$, where, R, $R^1$ and $R^2$ are as defined above.

The linker may or may not be an epoxide-containing compound. In one embodiment, when the linker is an epoxide containing compound, the linker may have a general formula (Ia):

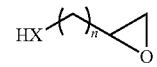

wherein:

X is selected from NH, NR, O, S, Se, COO, $CONR^1R^2$, CONRO, CONH and CONR; $R^1$ and $R^2$ are independently selected from the group consisting of hydrogen, optionally substituted alkyl, optionally substituted alkenyl, optionally substituted alkynyl, optionally substituted aryl and optionally substituted heteroaryl; and n is an integer from 0 to 25.

In another embodiment the epoxide-containing linker has the general formula (Ib):

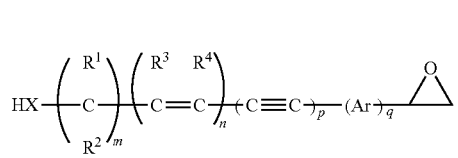

formula (Ib)

wherein:

X is selected from NH, NR, NHO, NRO, O, S, Se, COO, CONH, CONR, CSS, COS, CONHO, CONRO, CONHNH, CONRNH, CONRNR, CNO, PH, PR;

R, $R^1$, $R^2$, $R^3$, $R^4$ are independently selected from the group consisting of hydrogen, optionally substituted alkyl, optionally substituted alkeny, optionally substituted alkynyl, optionally substituted aryl and optionally substituted heteroaryl; and m, n, p and q is an integer independently selected from 0 to 25.

The position of the groups

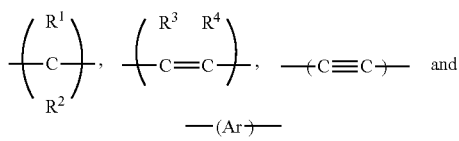

of formula (II) may be interchanged and these groups may also be present in more than one positions as will be understood by a skilled artisan.

In one embodiment, the variable X may also be any nucleophilic group that is capable of reacting with an epoxide group to form a chemical bond.

The epoxy-containing linker may comprise hydroxy-oxiranes. In one embodiment, the epoxy-containing linker is glycidol.

The disclosed method may also further comprise the steps of chemically coupling a subsequent electrophilic compound or ambiphilic compound to the preceding electrophilic compound directly or indirectly via the functional linker disclosed above. These additional steps of chemically coupling subsequent electrophilic compounds may be carried put repeatedly until the desired chain length is achieved. Advantageously, by repeating these steps, the number of electrophilic sites such as active oxirane sites for binding with the biological substances may increase, thereby increasing the probability and affinity of the biological substance to the substrate. In one embodiment, when the linker is an ambiphilic compound the linker comprises glycidol.

In one embodiment, the electrophilic compounds disclosed herein comprise epoxide containing compounds. For example, the first electrophilic compound and second electrophilic compound may be a first epoxide containing compound and a second epoxide containing compound. In one embodiment, at least one of the first epoxide containing-compound and the second epoxide containing-compound is an epihalohydrin. The epihalohydrin may be selected from the group consisting of, epichlorohydrin, epibromohydrin, and epiiodohydrin. In one embodiment, the method comprises selecting a poorly reactive substrate. The substrate may be selected from the group consisting of a polyester substrate, a polyamide substrate, an epoxy resin substrate, a polyacrylate substrate, a hydroxyl-functionalized substrate and a polysaccharide-based substrate. In one embodiment, the polysaccharide-based substrate is selected from the group consisting of cotton linters cotton pulp cotton fabrics cellulose fibers cellulose beads cellulose powder, microcrystalline cellulose, cellulose membranes, rayon, cellophane, cellulose acetate, cellulose acetate membranes, chitosan, chitin, dextran derivatives and agarose derivatives.

In one embodiment, the chemically coupling steps are undertaken at a temperature range of from about −30° C. to about 100° C., from about 0° C. to about 70° C., from about 4° C. to about 30° C. or from about 10° C. to about 27° C., from about 40° C. to about 70° C., from about 23° C. to about 35° C. and from about 23° C. to about 30° C.

The functional substances may be biologically active and may comprise biological substances and/or biomolecules. In one embodiment, the biological substances are enzymes. The method may comprise the step of chemically coupling an enzyme to said second electrophilic compound that has been coupled to the first electrophilic compound. The step of chemically coupling an enzyme to said second electrophilic compound may include providing stabilizing and activating additives such as sugars, thiols, antioxidants and chelators.

The enzyme may be selected from the group consisting of oxidoreductases, transferases, hydrolases, lyases, isomerases and ligases. Oxidoreductases catalyze oxidation-reduction reactions, and the substrate oxidized is regarded as hydrogen or electron donor. Transferases catalyze transfer of functional groups from one molecule to another. Hydrolases catalyze hydrolytic cleavage of various bonds. Lyases catalyze cleavage of various bonds by other means than by hydrolysis or oxidation, meaning for example that they catalyze removal of a group from or addition of a group to a double bond, or other cleavages involving electron rearrangement. Isomerases catalyze intramolecular rearrangement, meaning changes within one molecule. Ligases catalyze reactions in which two molecules are joined.

In one embodiment, the enzymes are oxidoreductases, which may act on different groups of donors, such as the CH—OH group, the aldehyde or oxo group, the CH—CH group, the CH—NH$_2$ group, the CH—NH group, NADH or NADPH, nitrogenous compounds, a sulfur group, a heme group, diphenols and related substances, hydrogen, single donors with incorporation of molecular oxygen, paired donors with incorporation or reduction of molecular oxygen or others. Oxidoreductases may also be acting on CH$_2$ groups or X—H and Y—H to form an X—Y bond. Typically enzymes belonging to the group of oxidoreductases may be referred to as oxidases, oxygenases, hydrogenases, dehydrogenases, reductases or the like. Exemplary oxidoreductases includes oxidases such as malate oxidase, glucose oxidase, hexose oxidase, aryl-alcohol oxidase, alcohol oxidase, long-chain alcohol oxidase, glycerol-3-phosphate oxidase, poly vinyl-alcohol oxidase, D-arabinono-1,4-lactone oxidase, D-mannitol oxidase, xylitol oxidase, oxalate oxidase, carbon-monoxide oxidase, 4-hydroxyphenylpyruvate oxidase, dihydrouracil oxidase, ethanolamine oxidase, L-aspartate oxidase, sarcosine oxidase, urate oxidase, methanethiol oxidase, 3-hydroxyanthranilate oxidase laccase, catalase, fatty-acid peroxidase, peroxidase, diarylpropane peroxidase, ferroxidase, pteridine oxidase, columbamine oxidase and the like. Oxidoreductases may also include oxygenases such as catechol 1,2-dioxygenase, gentisate 1,2-dioxygenase, homogentisate 1,2-dioxygenase, lipoxygenase, ascorbate 2,3-dioxygenase, 3-carboxyethylcatechol 2,3-dioxygenase indole 2,3-dioxygenase, caffeate 3,4-dioxygenase, arachidonate 5-lipoxygenase, biphenyl-2,3-diol 1,2-dioxygenase, linoleate 11-lipoxygenase, acetylacetone-cleaving enzyme, lactate 2-monooxygenase, phenylalanine 2-monooxygenase, inositol oxygenase and the like. Oxidoreductases may also include dehydrogenases such as alcohol dehydrogenase, glycerol dehydrogenase, propanediol-phosphate dehydrogenase, L-lactate dehydrogenase D-lactate dehydrogenase, glycerate dehydrogenase, glucose 1-dehydrogenase, galactose 1-dehyarogenase, allyl-alcohol dehydrogenase, 4-hydroxybutyrate dehydrogenase, octanol dehydrogenase, aryl-alcohol dehydrogenase, cyclopentanol dehydrogenase, long-chain-3-hydroxyacyl-CoA dehydrogenase, L-lactate dehydrogenase, D-lactate dehydrogenase, butanal dehydrogenase, terephthalate 1,2-cis-dihydrodiol dehydrogenase, succinate dehydrogenase, glutamate dehydrogenase, glycine dehydrogenase, hydrogen dehydrogenase, 4-cresol dehydrogenase, phosphonate dehydrogenase and the like. Reductases belonging to the group of oxidoreductases may also include enzymes such as diethyl 2-methyl-3-oxosuccinate reductase, tropinone reductase, long-chain-fatty-acyl-CoA reductase, carboxylate reductase, D-proline reductase, glycine reductase, Heme-proteins such as cytochromes and the like. In one embodiment, the enzymes are lyases, which may belong to either of the following groups: carbon-carbon lyases, carbon-oxygen lyases, carbon-nitrogen lyases, carbon-sulfur lyases, carbon-halide lyases, phosphorus-oxygen lyases and other lyases.

The carbon-carbon lyases may also include carboxy-lyases, aldehyde-lyases, oxo-acid-lyases and others. Some specific examples belonging to these groups are oxalate decarboxylase, acetolactate decarboxylase, aspartate 4-decarboxylase, lysine decarboxylase, aromatic-L-amino-acid decarboxylase, methylmalonyl-CoA decarboxylase, carnitine decarboxylase, indole-3-glycerol-phosphate synthase, gallate decarboxylase, branched-chain-2-oxoacid, decarboxylase, tartrate decarboxylase, arylmalonate decarboxylase, fructose-bisphosphate aldolase, 2-dehydro-3-deoxy-phosphogluconate aldolase, trimethylamine-oxide aldolase, propioin synthase, lactate aldolase, vanillin synthase, isocitrate lyase, hydroxymethylglutaryl-CoA lyase, 3-hydroxyaspartate aldolase, tryptophanase, deoxyribodipyrimidine photo-lyase, octadecanal decarbonylase and the like.

The carbon-oxygen lyases may include hydro-lyases, lyases acting on polysaccharides, phosphates and others. Some specific examples are carbonate dehydratase, fumarate hydratase, aconitate hydratase, citrate dehydratase, arabinonate dehydratase, galactonate dehydratase, altronate dehydratase, mannonate dehydratase, dihydroxy-acid dehydratase, 3-dehydroquinate dehydratase, propanediol dehydratase, glycerol dehydratase, maleate hydratase, oleate hydratase, pectate lyase, poly(β-D-mannuronate) lyase, oligogalacturonide lyase, poly(α-L-guluronate) lyase, xanthan lyase, ethanolamine-phosphate phospho-lyase, carboxymethyloxysuccinate lyase and the like.

The carbon-nitrogen lyases may include ammonia-lyases, lyases acting on amides amidines, etc., amine-lyases and the like. Specific examples of these groups of lyases are aspartate ammonia-lyase, phenylalanine ammonia-lyase, ethanolamine ammonia-lyase, glucosaminate ammonia-lyase, argininosuccinate lyase, adenylosuccinate lyase, ureidoglycolate lyase and 3-ketovalidoxylamine C—N-lyase.

The carbon-sulfur lyases may include dimethylpropio-thetin dethiomethylase, alliin lyase, lactoylglutathione lyase and cysteine lyase.

The carbon-halide lyases may include 3-chloro-D-alanine dehydrochlorinase and dichloromethane dehalogenase.

The phosphorus-oxygen lyases may include adenylate cyclase, cytidylate cyclase, glycosylphosphatidylinositol diacylglycerol-lyase.

In another embodiment, the enzymes are hydrolases selected from the group consisting of glycosylases, enzymes acting on acid anhydrides and enzymes acting on specific bonds such as ester bonds ether bonds carbon-nitrogen bonds, peptide bonds, carbon-carbon bonds, halide bonds, phosphorus-nitrogen bonds, sulfur-nitrogen bonds, carbon-phosphorus bonds, sulfur-sulfur bonds or carbon sulfur bonds.

The glycosylases may be glycosidases which are capable of hydrolysing O- and S-glycosyl compounds or N-glycosyl compounds. The glycosylases may also include α-amylase β-amylase, glucan 1,4-α-glucosidase, cellulase, endo-1,3(4)-β-glucanase, inulinase, endo-1,4-β-xylanase oligo-1,6-glucosidase, dextranase, chitinase, pectinase, polygalacturonase, lysozyme, levanase, quercitrinase, galacturan 1,4-α-galacturonidase, isoamylase, glucan 1,6-αglucosidase, glucan endo-1,2-β-glucosidase, licheninase, agarase, exo-poly-α-galacturonosidase, κ-carrageenase, steryl-β-glucosidase, strictosidine β-glucosidase, mannosyl-oligosaccharide glucosidase, lactase, oligo-xyloglucan β-glycosidase, polymannuronate hydrolase, chitosanase, poly(ADP-ribose) glycohydrolase, purine nucleosidase, inosine nucleosidase, uridine nucleosidase, adenosine nucleosidase, and the like.

The enzymes acting on acid anhydrides may be for example those acting on phosphorus- or sulfonyl-containing anhydrides. Exemplary enzymes acting on acid anhydrides are include inorganic diphosphatase, trimetaphosphatase, adenosine-triphosphatase, apyrase, nucleoside-diphosphatase, acylphosphatase, nucleotide diphosphatase, endopolyphosphatase, exopolyphosphatase, nucleoside phospho-acylhydrolase, triphosphatase, CDP-diacylglyceroldiphosphatase, undecaprenyldiphosphatase, dolichyldiphosphatase, oligosaccharide-diphosphodolichol diphosphatase, heterotrimeric G-protein GTPase, small monomeric GTPase, dynamin GTPase, tubulin GTPase, diphosphoinositolpolyphosphate diphosphatase, $H^+$-exporting ATPase, monosaccharide-transporting ATPase, maltose-transporting ATPase, glycerol-3-phosphate-transporting ATPase, oligopeptide-transporting ATPase, polyamine-transporting ATPase, peptide-transporting ATPase, fatty-acyl-CoA-transporting ATPase, protein-secreting ATPase and the like.

The enzymes acting on the ester bonds may include esterases, lipases, carboxylic ester hydrolases, thiolester hydrolases, phosphoric ester hydrolases, sulfuric ester hydrolases and ribonucleases. Exemplary enzymes acting on ester bonds include acetyl-CoA hydrolase, palmitoyl-CoA hydrolase, succinyl-CoA hydrolase, 3-hydroxyisobutyryl-CoA hydrolase, hydroxy-methylglutaryl-CoA hydrolase, hydroxyacylglutathione hydrolase, glutathione thiolesterase, formyl-CoA hydrolase, acetoacetyl-CoA hydrolase, S-formylglutathione hydrolase, 5-succinylglutathione hydrolase, oleoyl-[acyl-carrier-protein]hydrolase, ubiquitin thiolesterase, [citrate-(pro-35)-lyase]thiolesterase, (S)-methylmalonyl-CoA hydrolase, ADP-dependent short-chain-acyl-CoA hydrolase, ADP-dependent medium-chain-acyl-CoA hydrolase, acyl-CoA hydrolase, dodecanoyl-[acyl-carrier protein]hydrolase, palmitoyl-(protein) hydrolase, 4-hydroxy-benzoyl-CoA thioesrerase, 2-(2-hydroxyphenyl)benzene-sulfinate hydrolase, alkaline phosphatase, acid phosphatase, phosphoserine phosphatase, phosphatidate phosphatase, 5'-nucleotidase, 3'-nucleotidase, 3'(2'),5'-bisphosphate nucleotidase, 3-phytase, glucose-6-phosphatase, glycerol-2-phosphatase, phosphoglycerate phosphatase, glycerol-1-phosphatase, mannitol-1-phosphatase, sugar-phosphatase, sucrose-phosphatase, inositol-1 (or 4)-mono-phosphatase, 4-phytase, phosphatidyiglycero-phosphatase, ADP phophoglycerate phosphatase, N-acyl-neuraminate-9-phosphatase, nucleotidase, polynucleotide 3'-phosphatase, glycogen-synthase-D phosphatase, pyruvate dehydrogenase (lipoamide) phosphatase, acetyl-CoA carboxylase phosphatase, 3-deoxy-manno-octulosonate-8-phosphatase, polynucleotide 5'-phosphatase, sugar-terminal-phosphatase, alkylacetyiglycerophosphatase, 2-deoxyglucose-6-phosphatase, glucosylglycerol 3-phosphatase, 5-phytase, phosphodiesterase I, glycerophospho-choline phosphodiesterase, phospholipase C, phospholipase D, phosphoinositide phospholipase C, sphingomyelin phosphodiesterase, glycerophosphocholine cholinephospho-diesterase, alkylglycerophosphoethanolamine phospho diesterase, glycerophosphoinositol glyce-rophospho-diesterase, arylsulfatase, steryl-sulfatase, glyco-sulfatase, choline-sulfatase, cellulose-polysulfatase, monomethyl-sulfatase, D-lactate-2-sulfatase, glucuronate-2-sulfatase, prenyl-diphosphatase, aryldialkyiphosphatase, diisopropyl-fluorophosphatase, oligonucleotidase, poly(A)-specific ribonuclease, yeast ribonuclease, deoxy-ribonublease (pyrimidine dimer), Physarum polycephalum ribonuclease, ribonculease alpha, Aspergillus nuclease S1, Serratia marcescens nuclease, carboxylesterase, arylesterase, triacyiglycerol lipase, phospholipase A2, lysophospholipase, acetylesterase, acetyicholinesterase, cholinesterase, tropinesterase, pectinesterase, sterol esterase, chiorophyllase, L-arabinonolactonase, glucono-lactonase, uronolactonase, tannase, retinyl-palmitate esterase, hydroxybutyrate-dimer hydrolase, acylglycerol lipase, 3-oxoadipate enol-lactonase, 1,4-lactonase, galactolipase, 4-pyridoxolactonase, acylcarnitine hydrolase, aminoacyl-tRNA hydrolase, D-arabinono-lactonase, 6-phosphogluconolactonase, phospholipase A1, 6-acetylglucose deacetylase, lipoprotein lipase, dihydrocoumarin hydrolase, limonin-D-ring-lactonase, steroid-lactonase, triacetate-lactonase, actinomycin lactonase, orsellinate-depside hydrolase, cephalosporin-C deacetylase, chiorogenate hydrolase, α-amino-acid esterase, 4-methyloxaloacetate esterase, carboxy-methylenebutenolidase, deoxylimonate-A-ring-lactonase, 1-alkyl-2-acetylglycerophosphocholine esterase, fusarinine-C-ornithinesterase, sinapine esterase, wax-ester hydrolase, phorbol-diester hydrolase, phosphatidylinositol deacylase, sialate 0-acetylesterase, acetoxybutynyl-bithiophene deacetylase, acetylsalicylate deacetylase, methylumbelliferyl-acetate deacetylase, 2-pyrone-4,6-dicarboxylate lactonase, N-acetylgalactosaminoglycan deacetylase, juvenile-hormone esterase, bis(2-ethyl-hexyl)phthalate esterase, proteinglutamate methyl-esterase, 11-cis-retinyl-palmitate hydrolase, all-trans-retinyl-palmitate hydrolase, L-rhamnono-1,4-lactonase, 5-(3,4-diacetoxybit-1-ynyl)-2,2'-bithiophene deacetylase, fatty-acyl-ethyl-ester synthase, xylono-1,4-lactonase, cetraxate benzylesterase, acetylalkyiglycerol acetylhydrolase, acetylxylan esterase, feruloyl esterase, cutinase, poly(3-hydroxybutyrate) depolymerase, poly(3-hydroxyoctanoate), depolymerase acyloxyacyl hydrolase, acyloxyacyl hydrolase, polyneuridine-aldehyde esterase and the like The enzymes acting on ether bonds may include trialkylsulfonium hydrolases and ether hydrolases. Enzymes acting on ether bonds may act on both thioether bonds and on the oxygen equivalent. Specific enzyme examples belonging to these groups are adenosyihomocysteinase, adenosylmethionine hydrolase, isochorismatase, alkenyiglycerophosphocholine hydrolase, epoxide hydrolase, trarcs-epoxysuccinate hydrolase, alkenylglycerophosphoethanolamine hydrolase, leukotriene-A4 hydrolase, hepoxilin-epoxide hydrolase and limonene-1,2-epoxide hydrolase.

The enzymes acting on carbon-nitrogen bonds may hydrolyze linear amides, cyclic amides, linear amidines, cyclic amidines, linear carbamides (ureas), cyclic carbamides (ureas), nitriles and other compounds. Specific examples belonging to these groups are urease, amidase (acylase), asparaginase, glutaminase, ω-amidase, β-ureidopropionase, arylformamidase, biotinidase, aryl-acylamidase, aminoacylase, aspartoacylase, acetyl-ornithine deacetylase, acyllysine deacylase, succinyl-diaminopimelate desuccinylase, pantothenase, ceramidase, choloylglycine hydrolase, N-acetylglucosamine-6-phosphate deacetylase, N-acetylmuramoyl-L-alanine amidase, 2-(acetamidomethylene)succinate hydrolase, 5-aminopentan-amidase, formylmethionine deformylase, hippurate hydrolase, N-acetylglucosamine deacetylase, D-glutaminase, N-methyl-2-oxoglutaramate hydrolase, glutamin-(asparagin-)ase, alkylamidase, acylagmatine amidase, chitin deacetylase, peptidyl-glutaminase, N-carbamoylsarcosine amidase, N-(long-chain-acyl) ethanolamine deacylase, mimosinase, acetylputrescine deacetylase, 4-acetamidobutyrate deacetylase, theanine hydrolase, 2-(hydroxymethyl)-3-(acetamidomethylene) succinate hydrolase, 4-methyleneglutaminase, N-formylglutamate deformylase, glycosphingolipid deacylase, aculeacin-A deacylase, peptide deformylase, dihydropyrimidinase, dihydroorotase, carboxyrnethyl-hydantoinase, creatininase, L-lysine-lactamase, arginase, guanidinoacetase, creatinase, allantoicase, cytosine deaminase, riboflavinase, thiaminase, 1-aminocyclopropane-1-carboxylate deaminase and the like.

In one embodiment, the enzymes immobilized are enzymes acting on peptide bonds, which group is also referred to as peptidases. Peptidases can be further divided into exopeptidases that act only near a terminus of a polypeptide chain and endopeptidases that act internally in polypeptide chains. Enzymes acting on peptide bonds may include enzymes selected from the group of aminopeptidases, dipeptidases, di- or tripeptidyl-peptidases, peptidyl-dipeptidases, serine-type carboxypeptidases, metallocarboxypeptidases, cysteinetype carboxypeptidases, omega peptidases, serine endopeptidases, cysteine endopeptidases, aspartic endopeptidases, metalloendopeptidases and threonine endopeptidases. Some specific examples of enzymes belonging to these groups are cystinyl aminopeptidase, tripeptide aminopptidase, prolyl aminopeptidase, arginyl aminopeptidase, glutamyl aminopeptidase, cytosol alanyl aminopeptidase, lysyl aminopeptidase, Met-X dipeptidase, non-stereospecific dipeptidase, cytosol nonspecific dipeptidase, membrane dipeptidase, dipeptidase E, dipeptidyl-peptidase I, dipeptidyl-dipeptidase, tripeptidyl-peptidase I, tripeptidyl-peptidase II, X-Pro dipeptidyl-peptidase, peptidyl-dipeptidase A, lysosomal Pro-X carboxypeptidase, carboxypeptidase C, acylaminoacyl-peptidase, peptidyl-glycinamidase, β-aspartyl-peptidase, ubiquitinyl hydrolase 1, chymotrypsin, chymotrypsin C, metridin, trypsin, thrombin, plasmin, enteropeptidase, acrosin, α-Lytic endopeptidase, glutamyl endopeptidase, cathepsin G, cucumisin, prolyl oligopeptidase, brachyurin, plasma kallikrein, tissue kallikrein, pancreatic elastase, leukocyte elastase, chymase, cerevisin, hypodermin C, lysyl endopeptidase, endopeptidase La, γ-renin, venombin AB, leucyl endopeptidase, tryptase, scutelarin, kexin, subtilisin, oryzin, endopeptidase K, thermomycolin, thermitase, endopeptidase So, t-plasminogen activator, protein C (activated), pancreatic endopeptidase E, pancreatic elastase II, IgA-specific serine endopeptidase, u-plasminogen activator, venombin A, furin, myeloblasts, semenogelase, granzyme A, granzyme B, streptogrisin A, streptogrisin B, glutamyl endopeptidase II, oligopeptidase B, omptin, togavirin, flavivirin, endopeptidase Clp, proprotein convertase 1, proprotein convertase 2, lactocepin, assemblin, hepacivirin, spermosin, pseudomonalisin, xanthomonalisin, C-terminal processing peptidase, physarolisin, cathepsin B, papain, ficain, chymopapain, asclepain, clostripain, streptopain, actinidain, cathepsin L, cathepsin H, cathepsin T, glycyl endopeptidase, cancer procoagulant, cathepsin S, picornain 3 C, picornain 2 A, caricain, ananain stem bromelain, fruit bromelain, legumain, histolysain, caspase-1, gingipain R, cathepsin K, adenain, bleomycin hydrolase, cathepsin F, cathepsin O, cathepsin V, nuclear-inclusion-a endopeptidase, helper-component proteinase, proteinase K, L-peptidase, gingipain K, staphopain, separase, V-cath endopeptidase, cruzipain, calpain-1, calpain-2, pepsin A, pepsin B, gastricsin, chymosin, cathepsin D, nepenthesin, renin, Proopiomelanocortin converting enzyme, aspergillopepsin I, aspergillopepsin II, penicillopepsin, rhizopuspepsin, endothiapepsin, mucorpepsin, candidapepsin, saccharopepsin, rhodotorulapepsin, acrocylirdropepsin, polyporopepsin, pycnoporopepsin, scytalidopepsin A, scytalidopepsin B, cathepsin E, barrierpepsin, signal peptidase II, plasmepsin I, plasmepsin II, phytepsin, yapsin 1, thermopsin, prepilin peptidase, nodavirus endopeptidase, memapsin 1, memapsin 2, atrolysin A, microbial collagenase, leucolysin, stromelysin 1, meprin A, procollagen C-endopeptidase, astacin, pseudolysin, thermolysin, bacillolysin, aureolysin, coccolysin, mycolysin, gelatinase B, leishmanolysin, saccharolysin, gametolysin, serralysin, horrilysin, ruberlysin, bothropasin, oligopeptidase A, endothelin-converting enzyme, ADAM 10 endopeptidase and the like.

The enzymes acting on carbon-carbon bonds may include, but are not limited to oxaloacetase, fumarylacetoacetase, kynureninase, phloretin hydrolase, acylpyruvate hydrolase, acetylpyruvate hydrolase, β-diketone hydrolase, 2, 6-dioxo-6-phenylhexa-3-enoate hydrolase, 2-hydroxymuconate-semialdehyde hydrolase and cyclohexane-1,3-dione hydrolase.

The enzymes acting on halide bonds may include alkylhalidase, 2-haloacid dehalogenase, haloacetate dehalogenase, thyroxine deiodinase, haloalkane dehalogenase, 4-chlorobenzoate dehalogenase, 4-chlorobenzoyl-CoA dehalogenase, atrazine chlorohydrolase and the like.

The immobilized enzymes disclosed herein may also include enzymes acting on specific bonds such as phosphoamidase, N-sulfoglucosamine sulfohydrolase, cyclamate sulfohydrolase, phosphonoacetaldehyde hydrolase, phosphonoacetate hydrolase, trithionate hydrolase, UDP sulfoquinovose synthase and the like.

Preferably the enzymes are ureases. The enzyme may be chemically coupled to the second epoxide-containing compound that has been coupled to the first epoxide-containing compound. It may also be coupled directly to the first epoxy-containing compound.

The substrate obtained from the described method for immobilization of biological substances thereon has a ether-containing compound having one moiety coupled to a substrate and another moiety coupled to an epoxide-containing compound. The substrate may be used in a dialysis device such as a peritoneal dialysis device or a hemodialysis device. In one embodiment, the substrate is used in a sorbent of a hemodialysis device.

BRIEF DESCRIPTION OF DRAWINGS

The accompanying drawings illustrate a disclosed embodiment and serve to explain the principles of the disclosed embodiment. It is to be understood, however, that the drawings are designed for purposes of illustration only, and not as a definition of the limits of the invention.

FIG. 1b is a schematic showing another possible modified substrate that may be obtained from the same embodiment of the method shown in FIG. 1a.

DETAILED DESCRIPTION OF DRAWINGS

Figure 1A:
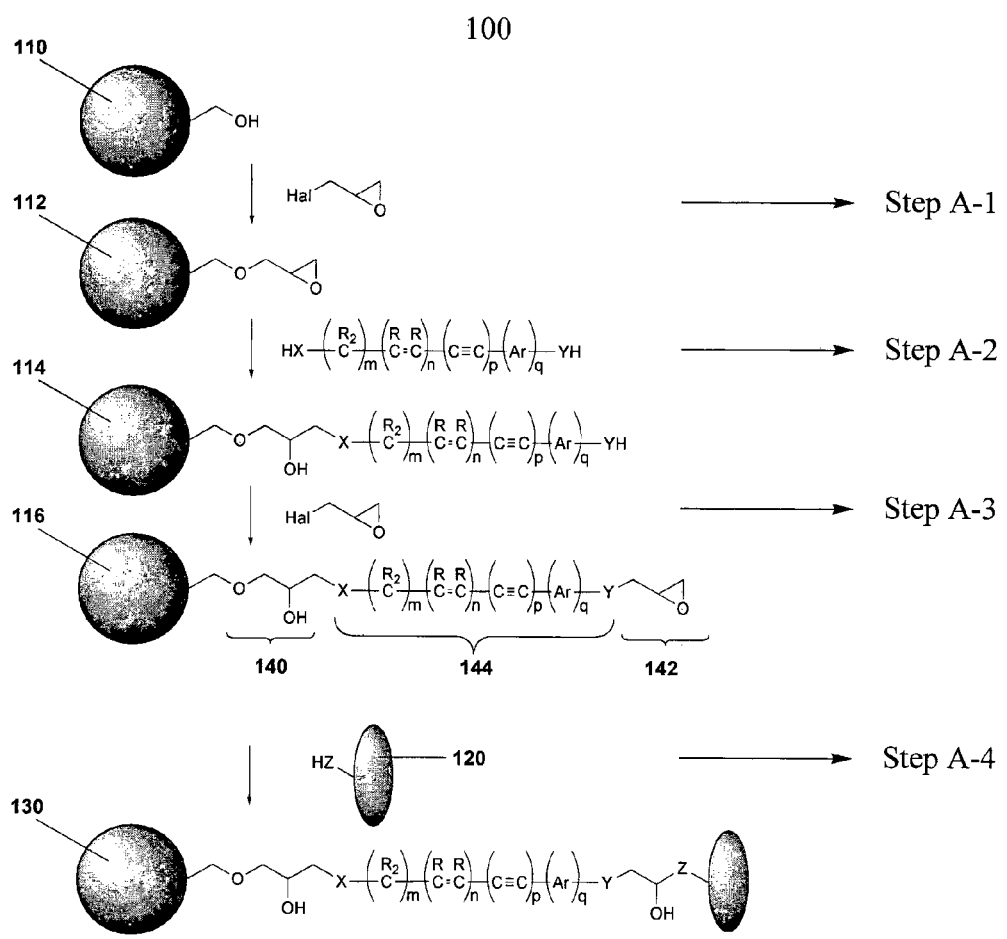
FIG. 1a is a schematic of one embodiment of the disclosed method of using di-nucleophilic linkers.

Referring to FIG. 1a there is shown a schematic of one embodiment of the disclosed method 100 of using di-nucleophilic linkers. A free (primary) hydroxyl group on the surface of an insoluble polymer 110 is first reacted with an epihalohydrin shown in step A-1. The reaction results in the release of the halogen on the epihalohydrin and a proton on the hydroxyl group, forming an ether bond, such that the resulting, modified substrate 112 is now chemically coupled to an epoxide group at the terminal end. The substrate 112 containing the epoxide group is then, in step A-2, reacted with a di-nucleophilic linker having the general formula (II), giving the linker modified substrate 114 as a product.

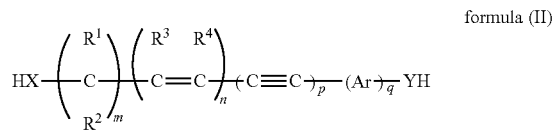

formula (II)

wherein:

X and Y are independently selected from NH, NR, NHO, NRO, O, S, Se, COO, CONH, CONR, CSS, COS, CONHO, CONRO, CONHNH, CONRNH, CONRNR, CNO, PH, PR;

R, R$^1$, R$^2$, R$^3$, R$^4$ are independently selected from the group consisting of hydrogen optionally substituted alkyl, optionally substituted alkenyl, optionally substituted alkynyl, optionally substituted aryl and optionally substituted heteroaryl; and m, n, p and q is an integer independently selected from 0 to 25.

After the reaction with the linker group in step A-2, the modified substrate 114 now contains the nucleophilic group Y at its terminal end. The nucleophilic group Y is then reacted in step A-3 with another epihalohydrin. Via nucleophilic substitution, the halogen present on the epihalohydrin is substituted by the nucleophilic group Y, resulting in the modified substrate 116 now having an ether moiety 140, a terminal epoxy moiety 142, that are respectively coupled by the linker 144. The epoxide terminal group of the modified substrate 116 is then reacted with a biological substance in the form of enzyme 120 that contains a nucleophilic group Z in step A-4. The enzyme becomes immobilized on the substrate to give the overall product 130. Stabilizers such as thiols may also be added in step A-4.

Figure 1B:
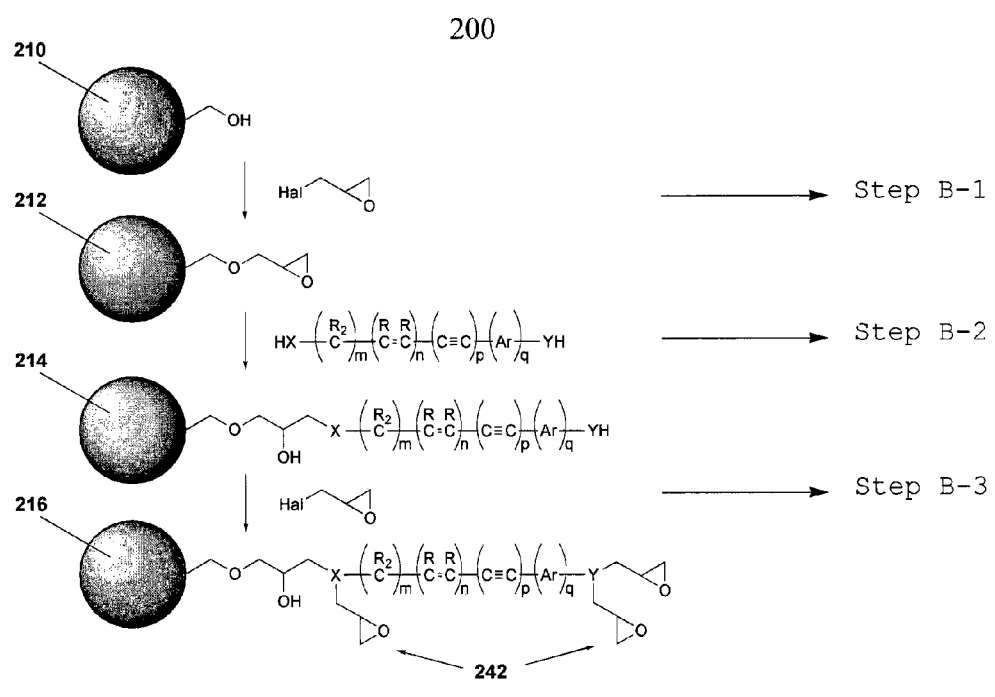

Referring to FIG. 1b there is shown a schematic 200 showing another product that may be obtained from the same embodiment of the method shown in FIG. 1a. The steps undertaken in FIG. 1b are the same as FIG. 1a. However in step B-3, more than one molecule of epihalohydrin undergoes nucleophilic substitution at both the nucleophilic groups X and Y, resulting in a substrate having multiple epoxide groups. Accordingly, the final modified substrate obtained (216) differs from modified substrate 116 in that the substrate 216 contains additional epoxy moieties 242 at nucleophilic groups X and Y. Modified substrate 216 can then undergo immobilization reactions similar to Step B-4 in FIG. 1a.

Figure 2:
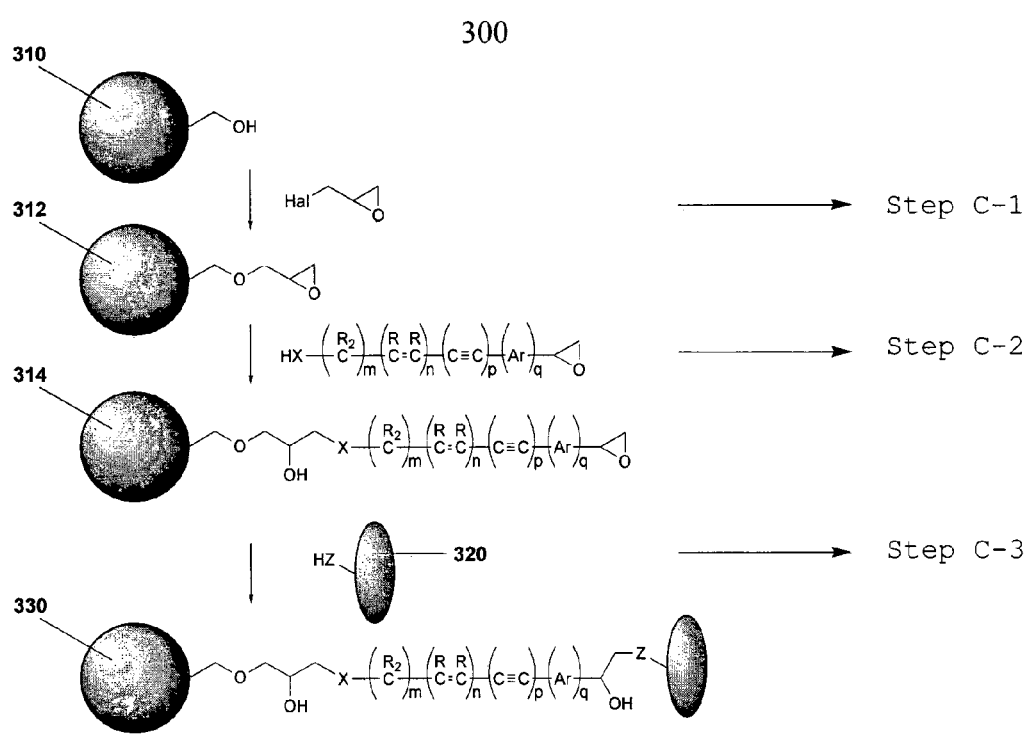
FIG. 2 is a schematic of another embodiment of the disclosed method using oxirane-functionalized linkers.

Referring to FIG. 2, there is shown a schematic of one embodiment of the disclosed method 300 using oxirane functionalized linkers. The substrate 310 containing a hydroxy group is first reacted with an epihalohydrin shown in step C-1. The reaction results in the release of the halogen on the epihalohydrin and hydrogen form the hydroxy group such that the resulting modified substrate 312 is now linked to an epoxide group at the terminal end. The substrate 312 containing the epoxide group is then in step C-2, reacted with at least one unit of an oxirane functionalized linker having the general formula (Ib):

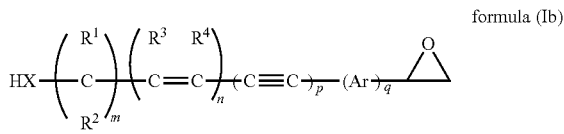

formula (Ib)

wherein:

X is selected from NH, NR, NHO, NRO, O, S, Se, COO, CONH, CONR, CSS, COS, CONHO, CONRO, CONHNH, CONRNH, CONRNR, CNO, PH, PR;

R, $R^1$, $R^2$, $R^3$, $R^4$ are independently selected from the group consisting of hydrogen, optionally substituted alkyl, optionally substituted alkenyl, optionally substituted alkynyl, optionally substituted aryl and optionally substituted heteroaryl; and m, n, p and q is an integer independently selected from 0 to 25.

After the reaction with the linker in step C-2, the resulting modified substrate 314 now contains the epoxide group of the oxirane functionalized linker at its terminal end. The epoxide terminal group is then reacted with a biological substance 320 that contains a nucleophilic group Z in step C-3. Eventually the biological substance is immobilized on the substrate to give the overall product 330.

Figure 3:
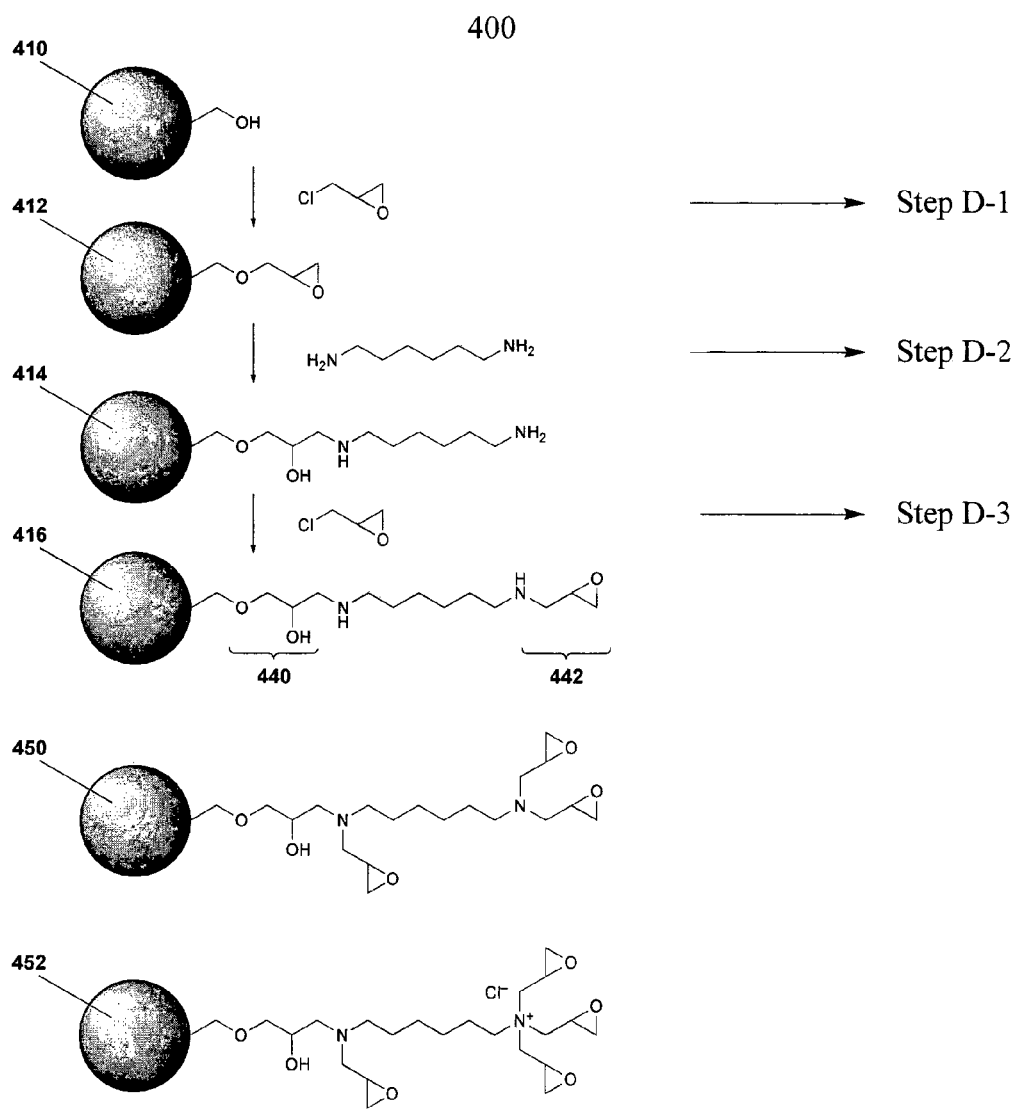
FIG. 3 is a schematic of a specific example of the method shown in FIG. 1a when hexanediamine is used as a linker and epichlorohydrin is used as the first and second epoxide containing compound.

Referring to FIG. 3 there is shown a schematic 400 of a specific example of the method shown in FIG. 1a, but when hexanediamine is used as a linker in step D-2 and epichlorohydrin is used as the first and second epoxide containing compound in steps D-1 and D-3. The resulting modified substrate contains one ether moiety 440 and at least one epoxy moiety 442, as exemplified in substrate 416. It may also contain multiple epoxy moieties, as shown in modified substrates 450 and 452.

Figure 4:
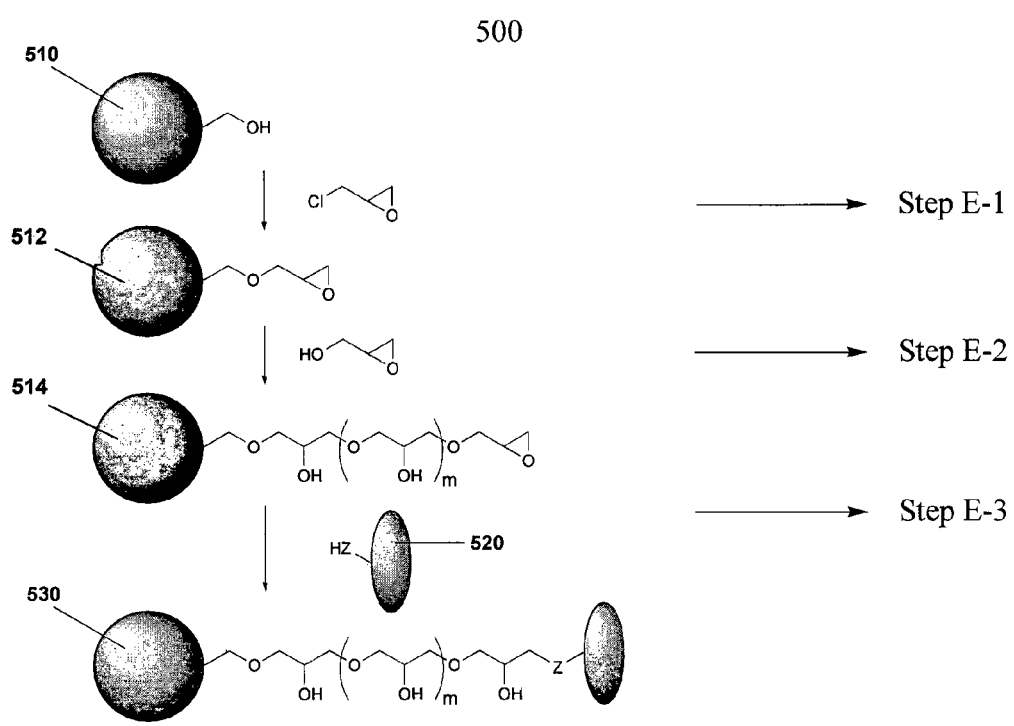
FIG. 4 is a schematic of a specific example of the method shown in FIG. 1b, when glycidol is used as a linker.

Referring to FIG. 4 there is shown a schematic 500 of a specific example of the method shown in FIG. 1b, when glycidol is used as a linker in step E-2. The resulting product obtained is indicated by reference numeral 514.

EXAMPLES

Non-limiting embodiments of the invention and a comparative example will be further described in greater detail by reference to specific Examples, which should not be construed as in any way limiting the scope of the invention.

Example 1

Preparation of Epoxy-Functionalized Substrate

Mercerization and epoxy-functionalization of cellulose was conducted by treating a vigorously stirred suspension of 5.0 g of cellulose in 100 ml of 2.4 M sodium hydroxide with 30 ml of epichlorohydrin at 55° C. for 4 h. The reaction mixture was filtered by suction and the solid residue ("primary epoxy cellulose") was washed with ultrapure water (3×50 ml). The epoxy group loading of dry primary epoxy cellulose was 125 µmol/g (see Table 1).

The primary epoxy-cellulose (15.3 g of wet material) was reacted with 15 ml of hexane-diamine (70% aqueous solution) in 100 ml of methanol at 23° C. for 4 h. The reaction mixture was filtered by suction and washed once with 100 ml of methanol to give 9.8 g of wet "amino cellulose". The presence of primary amino groups on the product was qualitatively assessed by its reaction with ninhydrin.

The amino cellulose (9.6 g of wet material) was then reacted with 30 ml of epichlorohydrin in 100 ml of methanol at 23° C. for 4 h. The reaction product ("secondary epoxy cellulose") was obtained by suction filtration and washing with cold water (3×100 ml). The epoxy group loading of dry secondary epoxy cellulose product was 108 µmol/g (see Table 1).

Method for the Determination of the Epoxy Group Loading

A sample of the epoxy group containing material (about 1 g of wet material) is suspended in 5 ml of water. The suspension is titrated with 0.01 N HCl to neutral pH if necessary. The neutral suspension is treated with 5 ml of 1.3 M aqueous sodium thiosulphate solution followed by incubation for 15 min with occasional shaking. The suspension is then titrated with 0.01 N HCl against bromophenol blue. The total amount of epoxy groups present in the sample is equivalent to the amount of HCl consumed in the titration. The epoxy loading of the dry material is calculated based on the known water contents (LOD) of the wet material. Representative experimental values are summarized in Table 1.

Example 2

Immobilization of Urease

The secondary epoxy cellulose prepared in Example 1 (12.5 g of wet material) was suspended in a cooled solution of Jack Bean urease (4.2 g) in 150 ml of 1.0 M potassium phosphate buffer at pH 7.5. The immobilization reaction was carried out in an incubator shaker at 4° C. for 24 h.

The reaction mixture was then filtered by suction and the residue ("immobilized urease") was washed 3 times with cold ultra pure water (3×150 ml).

Post-Immobilization Treatment of Immobilized Urease

The immobilized urease was soaked in an aqueous solution of cystein (5 mg/ml), ethylenediaminetetraacetic acid (EDTA, 1.0 mM) and glucose (0.2 g/ml) for 10 min, followed by suction filtration, and lyophilization for 24 h.

Comparative Example

Tables

TABLE 1

Comparison of epoxy group density of activated/modified cellulose, and commercial Eupergit ® C (Sigma-Aldrich)

|  | Epoxy loading after step D-1 (µmol/g) | Epoxy loading after step D-3 (µmol/g) | Eupergit (µmol/g) |
|---|---|---|---|
| Titration value | 125 | 108 | 260 |
| Commercial claimed value | N.A. | N.A. | ≧200 |

TABLE 2

Comparison of the activity of immobilized urease on activated/modified cellulose with and without amino linker

| Substrate | Activated cellulose with amino linker | Activated cellulose without amino linker |
|---|---|---|
| Activity of immobilized urease product (U/g) | 1100 | <100 |

TABLE 3

Comparison of activities of urease immobilized on a commercial substrate (Eupergit ® C) and on activated cellulose

| Substrate | Eupergit ® C | Activated cellulose |
|---|---|---|
| Activity of immobilized urease product (U/g) | 689 | 1850 |

APPLICATIONS

The disclosed method of preparing a substrate is a cost effective and efficient way of producing a substrate that is capable of immobilizing functional substances thereon. Advantageously, the method ensures that the substrate produced by the method allows the functional substances, such as enzymes, to be stably immobilized thereon. More advantageously, as the enzymes are stably attached to the substrate, the substrate can be reused repeatedly for long periods of time without substantially losing its enzymatic activity.

As the disclosed method can also work with low cost starting materials, the overall production costs can be substantially reduced if the method is used in large scale production of the substrates. Moreover, the chemical linker between the substrate such as a solid support and the functional substance is non-hydrolyzable. More advantageously, the inertness of the linker also attributes stability to the immobilized functional substance as the possibility of linker breakage due to undesirable chemical reactions is reduced.

The disclosed method also enables the user to vary the distance of the active oxirane groups from the substrate. When the active oxirane groups are at a suitable distance from the substrate, their reactivity towards the immobilization of functional substances may increase due to reduced steric hindrance. In addition, the linker may be chosen to ensure a high loading of reactive epoxide groups, which in turn translates to a high loading of functional substances. More advantageously, the linker may also be chosen such that it inherently possesses certain desired chemical properties. For example, when di-amine linkers are chosen, the final substrate obtained may have an inherent pH-buffering property. This is especially useful in applications like peritoneal dialysis where the lifespan and the efficacy of the sorbent may be adversely affected by a high or low pH.

The method also allows the easy post-assembly modification of off-the-shelf dialysis membranes such as cellulose-acetate based dialysers with urease. Urease can be immobilised after assembly, and can also be immobilised on one face of the membrane only.

The substrate obtained from the disclosed method also allows immobilization of the biological substance thereon to be carried out in a simple, robust and user friendly way. For example, the immobilization of a biological substance can be easily carried out at a laboratory level. This is so, because the immobilization of the biological substance can be carried out at ambient temperatures (e.g. room temperatures) in water/buffer solutions without requiring additional chemicals or reagents. Advantageously, the absence of additional chemicals or reagents significantly facilitates the purification of the immobilized product. The immobilized functional material obtained from the disclosed method can also be non-toxic, biodegradable and biocompatible. Advantageously, this allows the substrate to be used for medical applications, such as for example in dialysis applications as a sorbent to remove unwanted waste products from the human body. Furthermore, these properties also allow the product to be used in environmental applications such as water treatment, soil treatment, or waste treatment.

In addition, the disclosed method and substrate may also be useful in any one of the following applications: affinity chromatography, solid phase materials for chromatography (chiral), molecular imprinting, immobilizing dyes, sensors, biosensors, organic filters for selective toxin absorption, pharmaceutical applications (coating and binding), solid phase ion exchangers, solid phase metal scavengers and antioxidants.

While reasonable efforts have been employed to describe equivalent embodiments of the present invention, it will be apparent to the person skilled in the art after reading the foregoing disclosure, that various other modifications and adaptations of the invention may be made therein without departing from the spirit and scope of the invention and it is intended that all such modifications and adaptations come within the scope of the appended claims.

The invention claimed is:

1. A substrate comprising compounds disposed thereon coupled to a functional molecule, each compound having a chain comprising:
   a moiety R that is chemically coupled to the substrate, said moiety R being selected from the group consisting of an ether, ester, carbonyl, carbonate ester, thioether, disulfide, sulfinyl, sulfonyl, carbonothioyl, amine, amide, carbamide, ureas and guanidines; and
   an epoxide-containing moiety that is coupled to the moiety R by a linker comprising at least one nucleophilic group selected from the group consisting of an amine, hydroxyl group and thiol;
   wherein the functional molecule comprises an enzyme selected from the group consisting of urease, uricase, creatininase, lipases, esterases, cellulases, amylases, pectinases, catalases, acylase, catalase, esterase, penicillin amidase, and proteinase-K.

2. The substrate as claimed in claim 1, comprising an additional epoxide containing group coupled to the chain.

3. The substrate as claimed in claim 2, wherein the number of additional epoxide-containing groups is selected from the group consisting of 1, 2, 3, 4 and 5.

4. The substrate as claimed in claim 2, wherein at least one of the additional epoxide-containing groups is coupled to said chain by the nucleophilic group of said linker.

5. The substrate as claimed in claim 3, wherein said linker comprises additional nucleophilic groups to which said additional epoxide-containing groups are coupled to said chain.

6. The substrate as claimed in claim 5, wherein said additional epoxide-containing groups branch from the chain by coupling with the additional nucleophilic groups of said linker.

7. The substrate as claimed in claim 1, wherein the nucleophilic group of said linker is an amine.

8. The substrate as claimed in claim 1, wherein the linker is selected from the group consisting of saturated and unsaturated aliphatic and aromatic amines, diamines, and triamines.

9. The substrate as claimed in claim 8, wherein the aliphatic group of said amines is an alkyl group.

10. The substrate as claimed in claim 1, wherein the linker does contain an epoxide group.

11. The substrate as claimed in claim 1, wherein the linker comprises at least one of a di-nucleophilic species and a poly-nucleophilic species.

12. The substrate as claimed in claim 11, wherein the linker is selected from at least one of an alkyl-diamine and an alkene-diamine.

13. The substrate as claimed in claim 11, wherein the linker is selected from at least one of ethane-diamine, propane-diamine, butane-diamine, pentane-diamine, and hexane-diamine.

14. The substrate as claimed in claim 1, wherein the epoxide-containing compound is derived by reaction of an epihalohydrin with the at least one nucleophilic group of said linker.

15. The substrate as claimed in claim 1, wherein the substrate comprises a polymer.

16. The substrate as claimed in claim 15, wherein the polymer is a biocompatible polymer.

17. The substrate as claimed in claim 16, wherein the biocompatible polymer is selected from the group consisting of a polyester substrate, a polyamide substrate, a polyacrylate substrate, and a polysaccharide-based substrate.

18. The substrate as claimed in claim 17, wherein the polysaccharide-based substrate is selected from the group consisting of cotton linters, cotton pulp, cotton fabrics, cellulose fibers, cellulose beads, cellulose powder, microcrystalline cellulose, cellulose membranes, rayon, cellophane, cellulose, acetate, cellulose acetate membranes, chitosan, chitin, dextran derivatives and agarose derivatives.

19. The substrate as claimed in claim 15, wherein the polymer is a biopolymer.

20. The substrate as claimed in claim 1, further comprising a coating disposed on said substrate, the coating comprising a substantially homogenous mixture of stabilizing additives selected to stabilize said functional molecule.

21. The substrate as claimed in claim 20, wherein the stabilizing additives are selected from the group consisting of a sugar, an organic acid, an amino acid, a sugar acid and a thiol.

22. A sorbent cartridge for use in a dialysis device, the sorbent cartridge comprising a substrate as claimed in claim 1 for immobilizing urease.

23. A dialyzer for use in a dialysis device, the dialyzer comprising a substrate as claimed in claim 1 for immobilizing urease.

24. A dialysis method comprising the steps of:
exposing a dialysate containing urea to a substrate as claimed in claim 1; and
removing the dialysate from said substrate; wherein the substrate comprises an immobilized urease.

25. Use of the substrate as claimed in claim 1 in a dialysis device.

* * * * *